United States Patent [19]
Elhami

[11] Patent Number: 5,800,557
[45] Date of Patent: Sep. 1, 1998

[54] JOINT PROSTHESIS AND DEVICE FOR MAKING A DRILLING IN AT LEAST ONE JOINT HEAD

[76] Inventor: Laghaollah Elhami, Kafkastrasse 68, D-81737, Munich, Germany

[21] Appl. No.: 732,347

[22] PCT Filed: Apr. 18, 1995

[86] PCT No.: PCT/DE95/00481

§ 371 Date: Jan. 6, 1997

§ 102(e) Date: Jan. 6, 1997

[87] PCT Pub. No.: WO95/29650

PCT Pub. Date: Nov. 9, 1995

[30] Foreign Application Priority Data

May 2, 1994 [DE] Germany ............................ 44 15 378.3
Oct. 28, 1994 [DE] Germany ............................ 44 38 620.6

[51] Int. Cl.⁶ .................................................. A61F 2/36
[52] U.S. Cl. ............................................................ 623/23
[58] Field of Search ................................. 623/22, 23, 19; 606/67, 66, 65

[56] References Cited

U.S. PATENT DOCUMENTS

| 4,005,495 | 2/1977 | Locke et al. ........................... 623/18 |
| 4,274,164 | 6/1981 | Rehder .................................... 623/23 |

FOREIGN PATENT DOCUMENTS

| 493526 | 5/1950 | Belgium ................................. 623/23 |
| 99167 | 1/1984 | European Pat. Off. ................ 623/22 |
| 34787 | 12/1964 | German Dem. Rep. ............... 606/65 |
| 27 24 234 | 12/1977 | Germany ............................... 623/23 |
| 626 249 | 11/1981 | Switzerland .......................... 623/22 |
| 602171 | 4/1978 | U.S.S.R. ................................. 606/65 |
| 915844 | 3/1982 | U.S.S.R. ................................. 606/65 |
| 1593643 | 9/1990 | U.S.S.R. ................................. 606/65 |
| 1600756 | 10/1990 | U.S.S.R. ................................. 623/23 |
| 764600 | 12/1956 | United Kingdom .................. 623/23 |

*Primary Examiner*—David H. Willse
*Attorney, Agent, or Firm*—Sixbey, Friedman, Leedom & Ferguson; David S. Safran

[57] ABSTRACT

The invention relates to a joint prosthesis with a cap having a supporting surface, a telescopic arrangement having a telescopic component on a cap side and a telescopic component on a holder side and connected to a holder for securing to a bone surface, wherein the supporting surface is formed by an inner surface of the cap which is at least approximately shaped to fit the bone head. A restricting device acts dependently upon the direction so as to allow the cap to be moved in relation to the holder in a direction away from the socket and to prevent or at least hamper movement towards the socket. Also disclosed is a surgical device for making a drilling with a bush to accept an instrument and a system connected to the bush to accept the joint head at least partially; the median longitudinal axis of the bush is brought into relation with the periphery of the joint head in order to facilitate the positioning of the device in relation to the bone system.

53 Claims, 22 Drawing Sheets

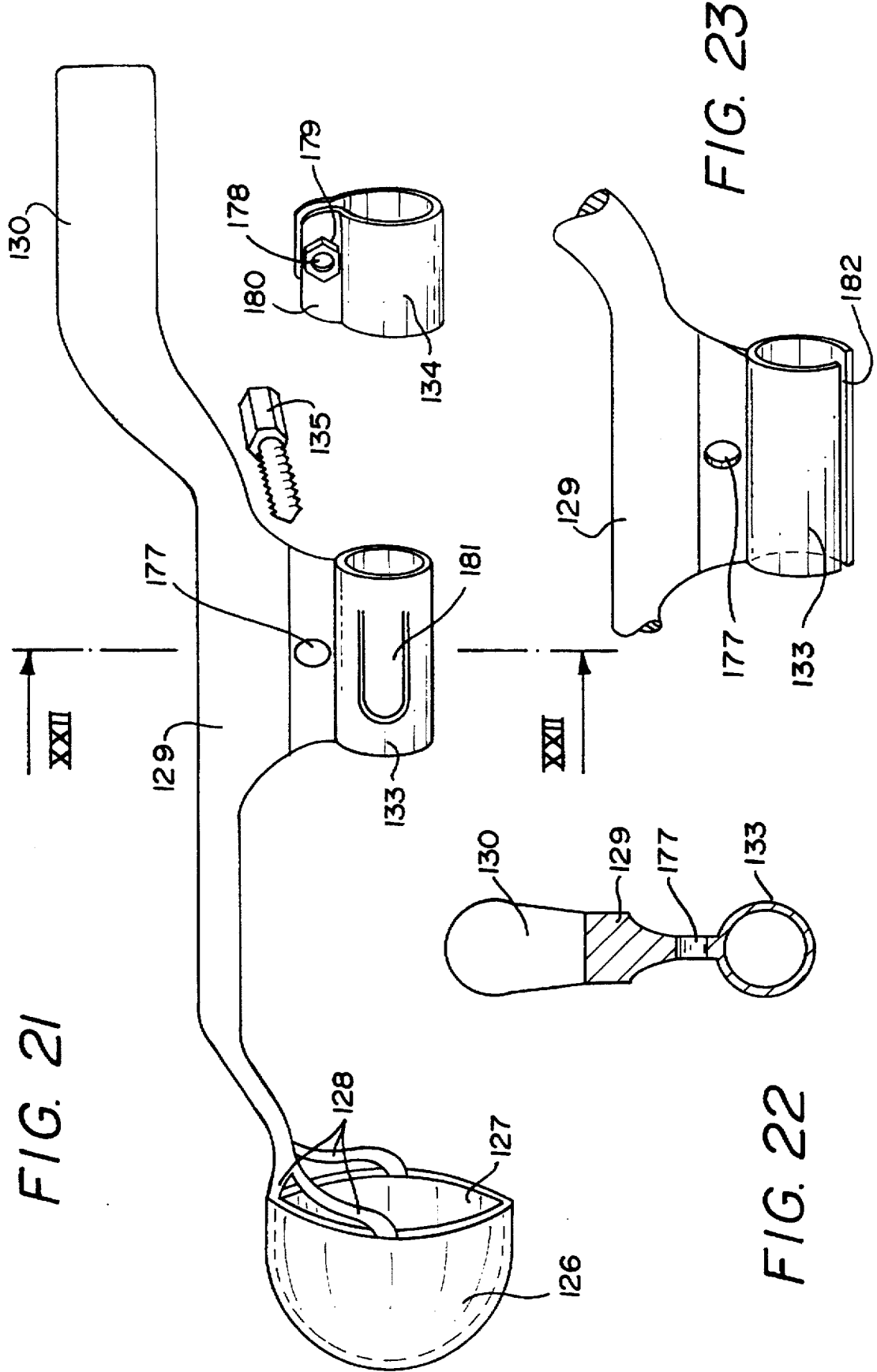

FIG. 24
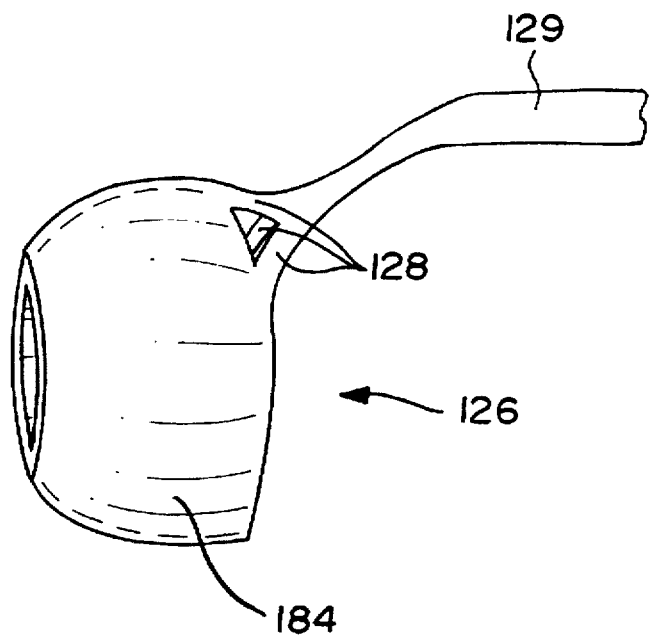
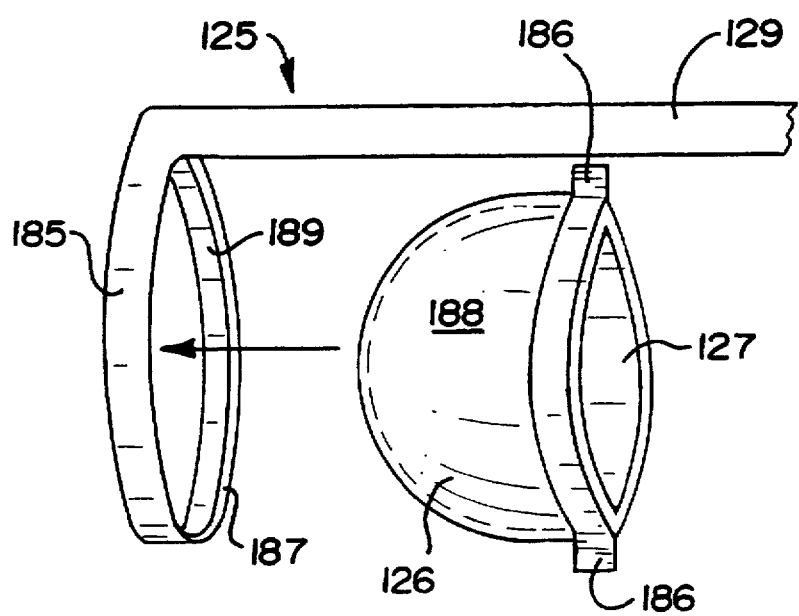
FIG. 25

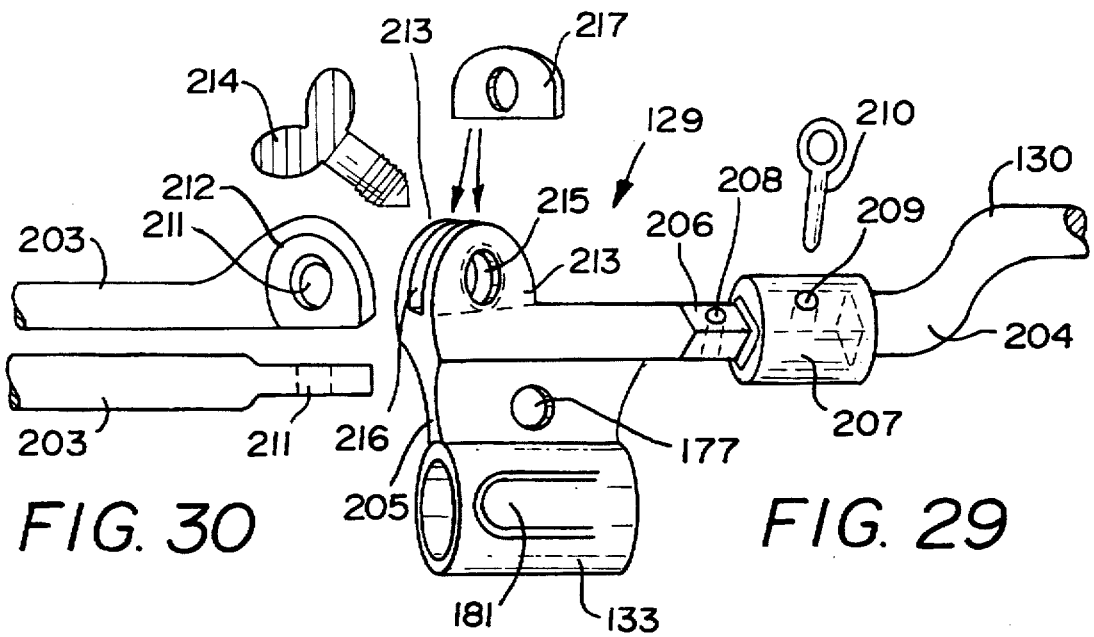
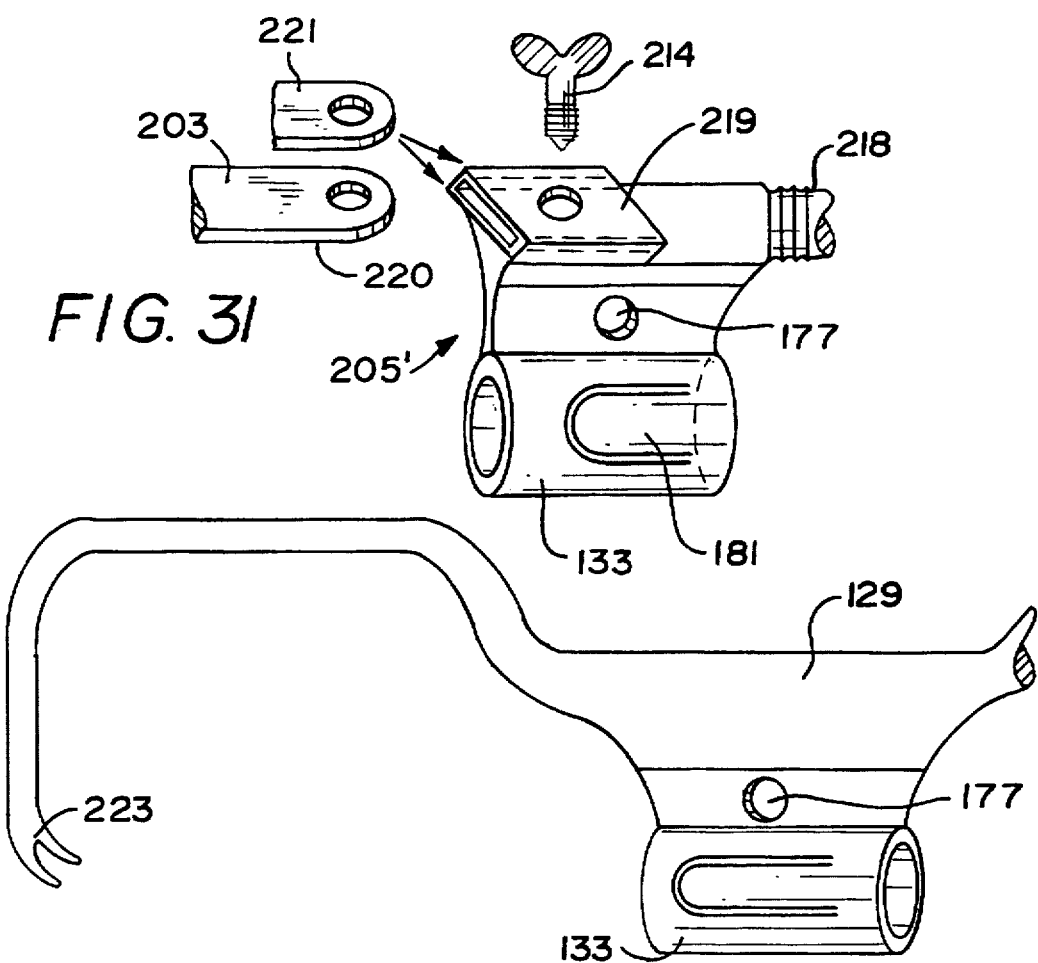

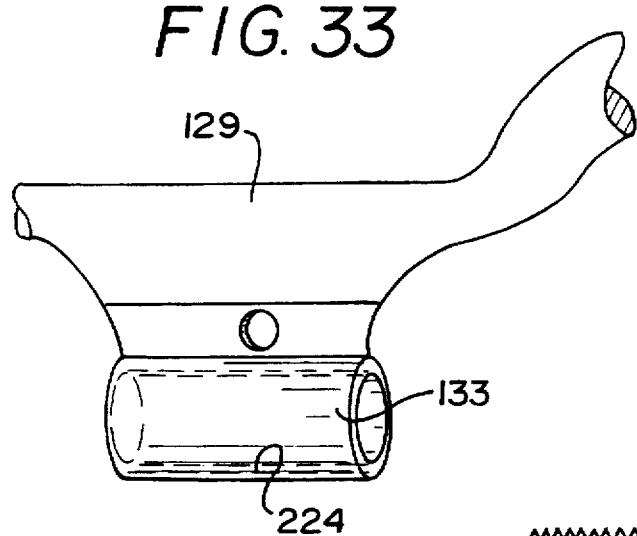
FIG. 33
FIG. 34
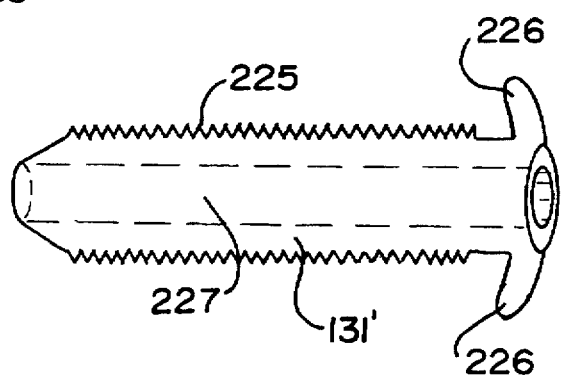
FIG. 35
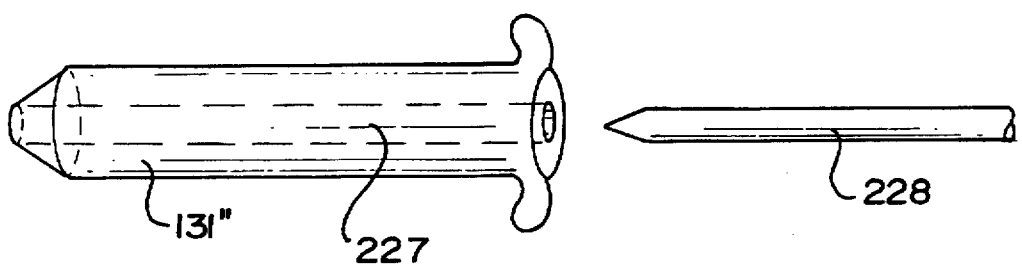
FIG. 36
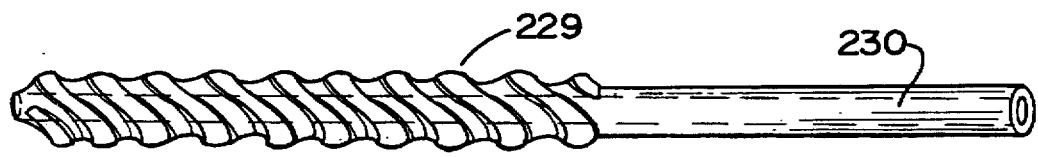
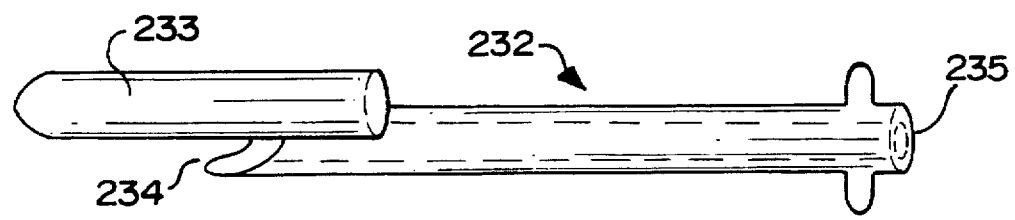
FIG. 37

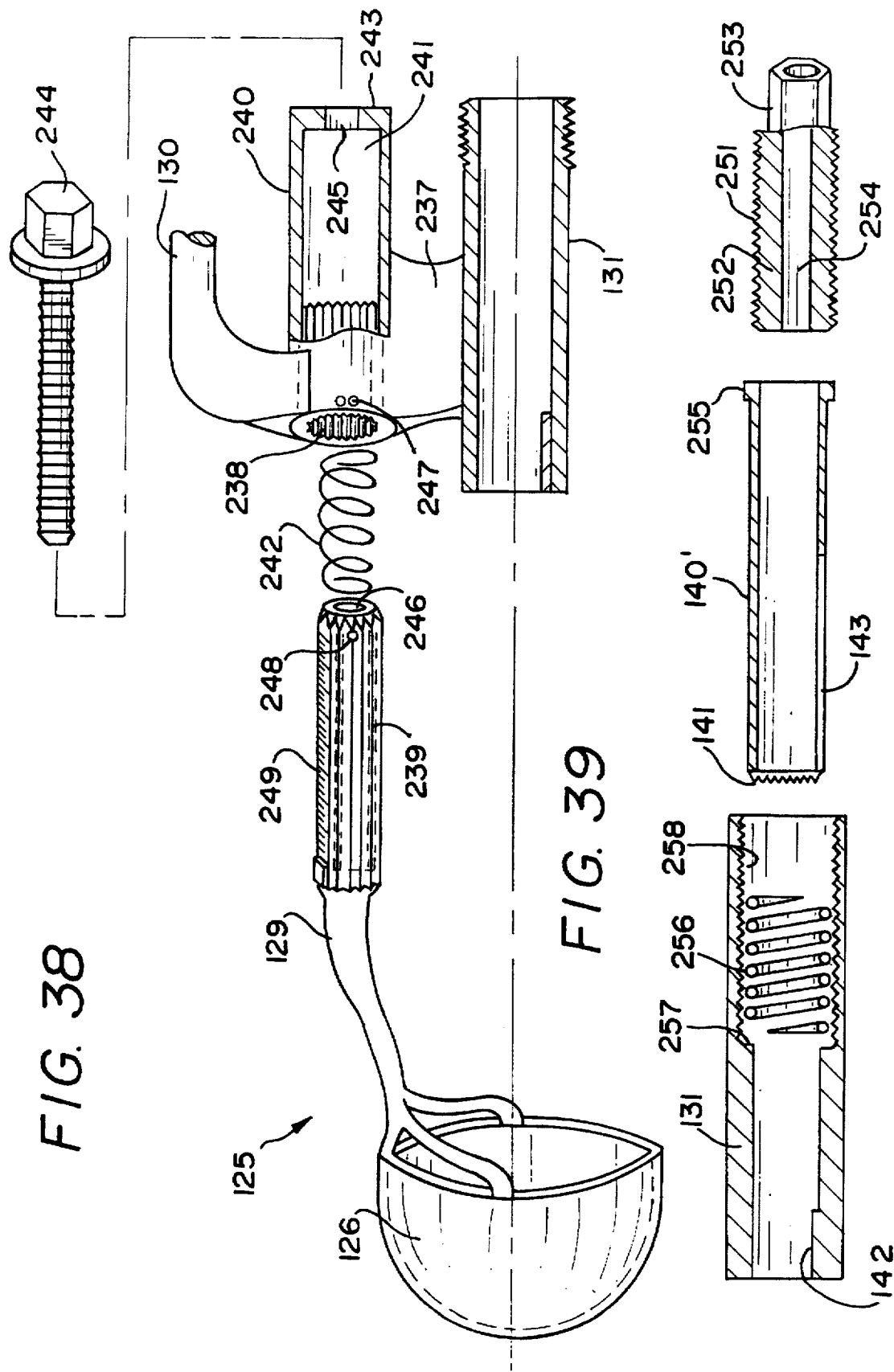

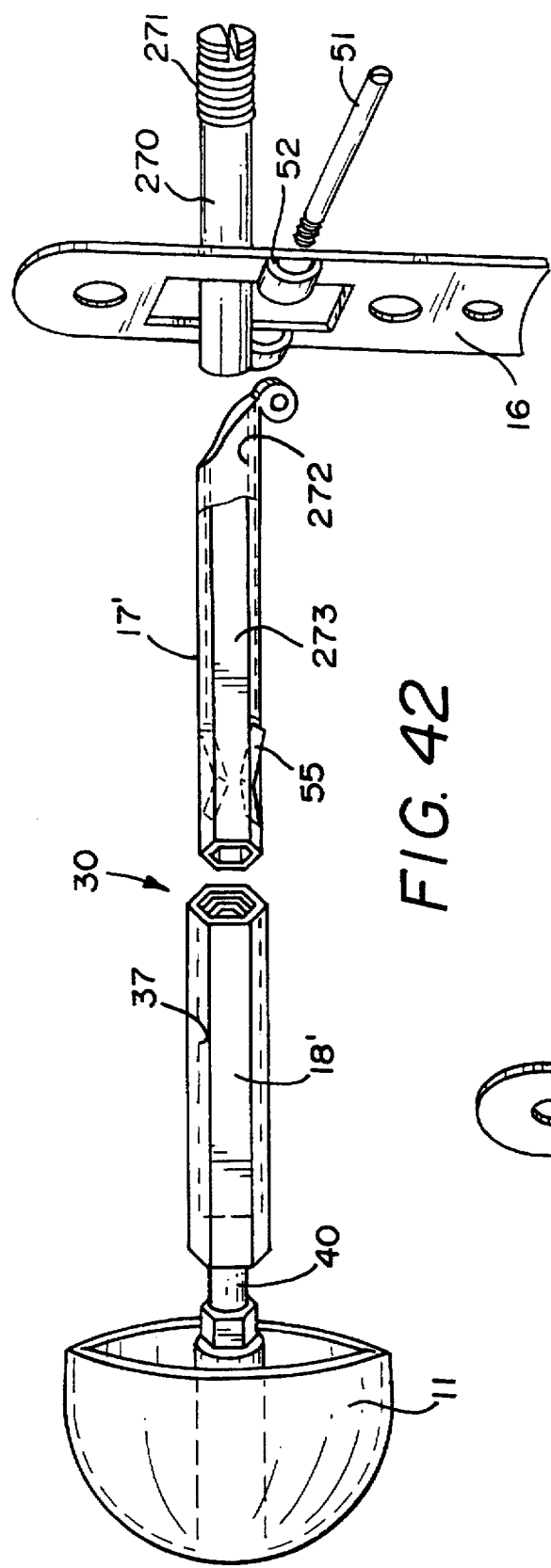
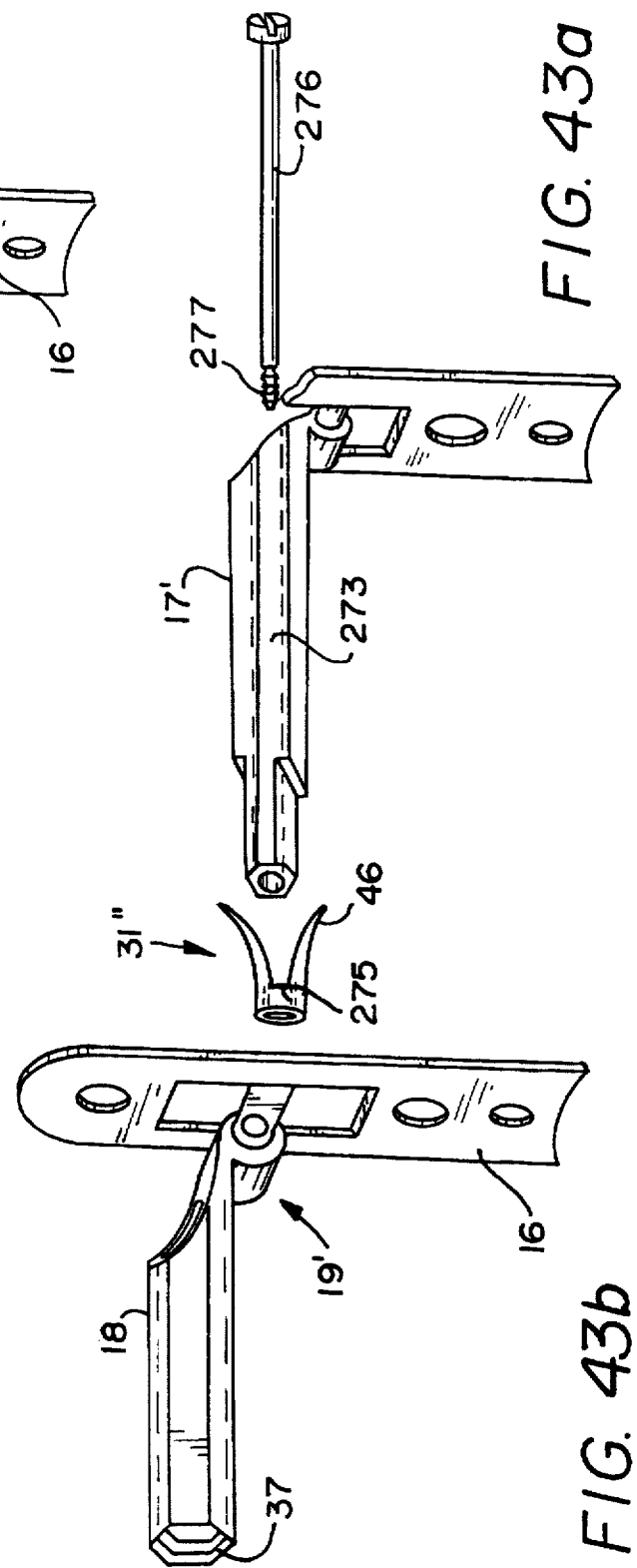

JOINT PROSTHESIS AND DEVICE FOR MAKING A DRILLING IN AT LEAST ONE JOINT HEAD

The invention relates to a joint prosthesis, and in particular to a joint prosthesis for a femoral head of a hip joint, which head cooperates with an acetabulum, as well as to a surgical device for making a drilling in at least one joint head.

A joint prosthesis of the type to which this invention is directed is known from the DE 35 38 346 A1. The cap of the known prosthesis is closed, at the bottom side thereof averted from the acetabulum, by a base with which the cap abuts a contact surface milled for this purpose in the femoral head. The fixing of the cap on the femoral head is effected with bone cement which is applied onto the milled contact surface. The cap-side telescopic member of this known prosthesis is a pin guided for free sliding movement in axial direction within a sleeve, which sleeve is fixed to the supporting member. The hold of the cap on the bone system is solely secured by the bone cement. Should this cement bond become loose in the course of time, the cap looses its hold.

The object of the invention is to provide for a joint prosthesis which can be simply, easily, and precisely implanted, which requires only slight, if any, machining of the joint head, like removal of pathological cartilage, and which is reliably protected against loosening even under a prolonged period of use.

This object is achieved by the features of the invention in a surprisingly simple manner.

By making use of the inner surface of the cap as the contact surface for the joint head the milling of a contact surface can be avoided. Veins supplying the joint head will remain preserved. By sparing removal of pathological cartilage the corticalis of the head is preserved what will provide for a solid contact surface for tile cap. The restraining means of the subject invention provides for safe anchoring of the cap in relation to the bone system without the necessity of the cap being cemented to the bone system. Particularly, lifting off of the cap from the joint head is prevented, while spontaneous contraction of the telescopic arrangement under the influence of pushing forces exerted on the cap or of additional tensile force applied by an optionally provided spring, respectively, is possible without any further ado.

The term "cap" presently is intended to also include a segment of a cap

In the case of the prosthesis known from DE 35 38 346 A1 the cap, the telescopic arrangement and the supporting member—except of the pin being sideably guided in the sleeve in longitudinal direction—altogether form a static system causing stiffening of the femoral head and of the neck of the femur with respect to the shaft of the femur. The known prosthesis therefore does not allow for biomechanical motions of the femur head and of the neck of the femur with respect to the shaft of the femur. Because of this there inevitably is a not insignificant osteoclasis of the femur in the area of the femur head and neck of the femur. This can be efficiently prevented, in conformity with a preferred further development of the invention, by a flexible and/or pivotal arrangement of the interconnection allowing for balancing of either pushing or pulling movements of the femoral head and the neck of the femur. Biomechanical motions of the femoral head and of the neck of the femur with respect to the shaft of the femur are thus enabled at least to a partial extent. Pushing, pulling, and shearing forces can therefore e.g. be transmitted by or introduced into the femur, whereby preservation of the bone and even new formation thereof can be reached. It is advisable to choose the elasticity and flexibility of the prosthesis so as to merely dimension or limit the elasticity and flexibility of the prosthesis to an extent excluding any possible risk of breaking of the femoral head or the neck of the femur in the prosthesis area.

Advantageous further developments of the joint prosthesis are the subject of to other aspects of the invention. Thus, hingedly connecting the telescopic arrangement to the supporting member or spring-elastically supporting the telescopic arrangement on the supporting member will foster natural biomechanical motions within the bone system, in particular movements of the femoral head in relation to the neck of the femur and of the neck of the femur in relation to the shaft of the femur. Additionally, extremely comfortable conditions will arise herewith, making the assembly, or setting of the prosthesis by a surgeon very easy. On finding a fracture within the femur in the vicinity of the femoral head, the provision of a locking means will allow for securing a motionless state of this area over a certain period of time.

A flexible member optionally may be incorporated in the area of the cap-side telescopic member and/or of the supporting member-side telescopic member. By positioning the flexible member to prevent twisting motion the cap is prevented from being exposed to any tilting forces and torques in the femoral head area which, after a short time, might result in a relative shift between the cap and the femur head. Furthermore it is ensured that the cap together with its anchoring equipment does not constitute a static system insensitive to tensional and compressive motions inside the femoral head, but rather a dynamic system adapted to respond to such pulling and pushing forces acting inside the femur bone. By designing the flexible member in a manner to prevent twisting motion, the cap is safeguarded against loosening and relative shifting with respect to the femoral head. A double- or multi-part design of at least one of the telescopic members will permit an individual adaption of the prosthesis to given conditions or to a special nature of the case without any problems, still in the course of surgical action. Moreover, it can be easily manufactured.

Facultative protection means against rotation will further assist in preventing any rotation of the cap in relation to the femoral head. Such rotation prevention means may be comprised amongst others by one or more protrusions, spines, etc. provided on the inner surface of the cap. The above rotation can also be prevented by eccentric positioning of the cap-side telescopic member or of the stem. The feature wherein the cap is equipped on its internal surface with at least one anti-twist member for preventing rotary motion of the cap relative to the femoral head will act against pain that might appear in certain motions as a result of tilting forces. The cap can be designed so that, the surface of the femoral head is permitted to get in contact with joint fluid. At the same time wear between the outer surface of the cap and the joint socket will become lower. An insert can be provided which will enable adjustment of the cap to tightly fit to a femoral head of given size and shape to thereby ensure a contact between cap and femur head which is almost without any clearance. By designing the cap in accordance with claim, the friction between the femoral head and the joint socket can be reduced. The cap with a flattened top is provided for an optional use the prosthesis without any artificial joint socket, whereby any possible protrusio acetabuli is prevented.

Structurally simplified joint prostheses are claimed.

The invention further relates to a surgical device of the type which is known from DE 35 38 346 A1. In the prior device, the contact member is an angled steel strip which is contacted with the femoral head like a slide calliper. The handling of the prior device is troublesome for the surgeon, since it requires numerous manipulations. Thus the contact member, upon being contacted with femoral head in the region of the fovea capitis femoris, is to be secured by an additional drilling and a fixing screw to prevent any displacement or slipping off after positioning and subsequent adjustment on the femoral head. Furthermore, the receiving sleeve for the drill, which is utilized as a drill jig sleeve, is to be aligned by means of an angle template which is to be put against the shaft of the femur. Nevertheless, the prior device does not permit to form a predetermined, exactly defined centric or in a predetermined manner eccentric bore through the femoral head irrespective of the periphery of the head. In this case, the position of the bore namely is solely determined by the positioning and adjustment of the head contact member, which are dependent on the surgeon's skill, and by the subsequent formation of the additional drilling for the fixing screw.

Therefore it is a further object of the invention to provide for a surgical device which not only is easy to handle but which also allows to form a precisely predetermined, axially aligned drilling which is centric or eccentric with respect to the joint head, substantially independently on the skill of the surgeon.

In the case of the device in accordance with the invention the handling is made decisively easier in that it is sufficient for an exact positioning and adjustment of the joint head relative to the central longitudinal axis of the drill to put the receiving means on the joint head. In view of the fact that the receiving means is designed to at least partially receive the joint head, a forced automatic relative alignment of the receiving means and of the joint head is attained. The additional insertion of a fixing screw may be dispensed with.

Three bearing points of the receiving member are sufficient for a defined alignment relative to the joint head. A receiving member in the form of a flat strap, for example in the manner of an annular body, may be manufactured particularly easily. In addition, such a flat strap forms a recess in the approximate front area of the outer surface of the joint head averted from the drill, which recess may be used for additionally checking the positioning and adjustment of the device. Due to this recess, a part of the outer surface of the joint head averted from the drill remains visible. Thus, for example the device, in surgical use, may be positioned on the femoral head for forming a drilling in the femur with such exactness that the fovea capitis femoris is concentrically surrounded by the flat strap.

Other features of the invention permit a simple and exact accommodation of the receiving means and of the receiving member, respectively, to different sizes and shapes of the joint heads when using one and the same device. The respective insert member may be received by the holding means via a latch or snap-in device or a similar device or by a corresponding screw device in a captive but always releasable manner.

Other features allow for an easy, exact and secure fixation of the device relative to the bone system in the course of the drilling operation, and features will make sure that the fixation of the device with respect to the bone system leaves the latter substantially unharmed. The centering sleeve being detachably fixed to the fixation sleeve essentially enhances the precision with which the bore can be made by the device of the invention. When using the centering sleeve, the intermediate sleeve has an inner diameter larger than the diameter of the guide channel of the centering sleeve in order to avoid any metallic contact between the drill and the inner wall of the intermediate sleeve, which contact otherwise would lead to the generation of heat and metal chips and would cause the infiltration of the fine metal chips into the bone system. A plurality of centering sleeves having different outer diameters may be provided, from which sleeves the appropriate one may be selected according to the outer diameter of the instrument used in the individual case. Other features provide for a particularly versatile applicability of the device in accordance with the invention.

Preferred embodiments of the invention are explained in more detail below with reference to the drawings, wherein FIG. 1 is a perspective exploded side view of a prosthesis in accordance with the invention;

FIG. 21 is a perspective exploded view of parts of the device of FIGS. 19 and 20;

FIG. 22 is a sectional view along line XXII—XXII of FIG. 21;

FIG. 23 is a partial view of the device comprising a modified embodiment of the pipe socket;

FIGS. 24 to 27 show modified embodiments of the receiving means;

FIG. 29 is a partial view of a modified embodiment of the device in accordance with the invention;

FIG. 30 is a top view of the portion carrying the receiving means in accordance with FIG. 29;

FIG. 31 is a view similar to FIG. 29 for a further modified embodiment of the device;

FIG. 32 shows a device similar to FIGS. 19 and 20 in which a sensor is provided instead of the receiving means;

FIGS. 33 and 34 show a partial view of the device comprising a modified embodiment of the pipe socket and a receiving sleeve adapted for being screwed into the pipe socket in accordance with FIG. 33;

FIG. 35 shows a modified embodiment of the receiving sleeve intended to receive a Kirschner's wire;

FIG. 36 is a perspective view of a drill adapted for use in connection with the Kirschner's wire of FIG. 35;

FIG. 37 is a perspective view of a chisel- or plane-shaped instrument;

FIG. 38 is an exploded, partially sectional view of a further modified embodiment of the device;

FIG. 39 is an exploded sectional view of parts of a further modified embodiment of the device;

FIG. 42 is a sectional view of a further modified embodiment of the prosthesis

FIGS. 43a and 43b are partial perspective views of other altered embodiments of the prosthesis according the invention.

Figure 1:
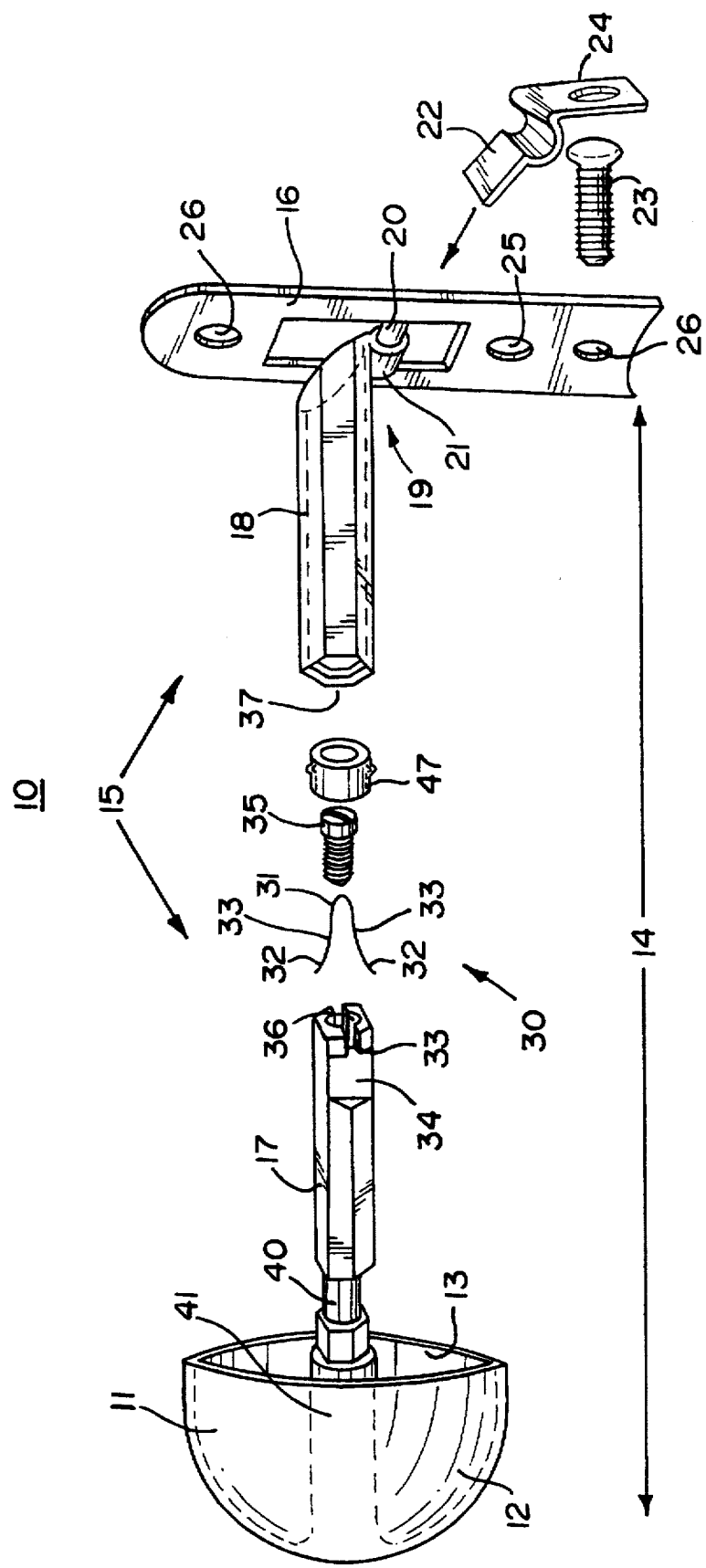

FIG. 1 shows a prosthesis 10 for a femoral head having a cap 11 the outer and inner surfaces 12 and 13 of which are approximately shaped like a spherical cap or calotte. The term "approximately shaped like a spherical cap or calotte" is intended to include cap shapes which are less than semi-spherical, as well as those shown in FIG. 1 and other figures, where the outline is semi-spherical or more than semi-spherical, or where a particular cylindrical or cone-like extension is attached to a semi-spherical body. In the implanted state of the prosthesis 10 the outer surface 12 of the cap 11 will be seated in an artificial or natural acetabulum (not shown), while the inner surface of the cap 13 at least partially abuts a suitably prepared femur head or the cartilage thereof, with the cap being locked against rotation. The cap 11 is held on the femur head by anchoring means 14, and it is anchored in relation to the shaft of the femur. The anchoring means 14 comprises a telescopic arrangement 15 and a supporting member, which in this example is a fixation plate 16.

The telescopic arrangement 15 includes a cap-side telescopic member and a supporting member-side telescopic member. In the embodiment of FIG. 1 the cap-side telescopic member is a male member 17, whereas the supporting member-side telescopic member is a female member 18. When the prosthesis is implanted, the male member 17 and the female member 18 telescopically engage each other, wherein the length of the telescopic arrangement 15 is dimensioned to pass through a bore drilled in the head, the neck, and the shaft of the femur. The female member 18 is connected to the supporting member 16 via a hinge 19. The axis of rotation of hinge 19 is defined by a crossbar 20 of the supporting member 16 and is substantially normal to the longitudinal extension of the supporting member 16. In the embodiment of FIG. 1 the end of the female member facing the supporting member 18 is fitted with a sleeving 21 which at least partly embraces crossbar 20. The female member 18 is elastically supported on supporting member 16 via a leaf spring 22. Leaf spring 22 abuts the outer surface of supporting member 16 as well as the bottom side of the female member 18; it is held by a screw 23 which extends through an opening 24 of the leaf spring and an opening 25 of the supporting member and which is screwed into the shaft of the femur. Further openings in the supporting member 16 for receiving fastening screws are indicated at 26.

Restraining means the operation of which is dependent on the direction of the forces acting thereon is integrated into anchoring means 14. In the embodiment of FIG. 1 the restraining means are defined by directionally dependent clutch or coupling, means in the form of snap-in locking, detent or latch means. Coupling means 30 includes a V-shaped spring 31 which terminates in two mutually opposite detents 32 projecting in opposite directions. Spring 31 is inserted into a groove 33 on the free end of male member 17. Flattened surfaces 34 in communication with groove 33 extend on both side of male member in the direction towards cap 11. Legs 32 of spring 31 are adapted to engage surfaces 34. Spring 31 is secured in groove 33 with a screw 35 which is screwed into a threaded longitudinal opening 36 in male member 17. The detents 32 of spring 31 will lean against mutually diametrically opposite contacting surfaces 37 on the inner side of female member 18. These contacting surfaces 37 are provided with a larger number of grooves shaped like a saw or similar in profile. Screw 35 can be loosened or set, even when the prosthesis is assembled, by a screw-driver, which is inserted into the interior of female member 18 from the end thereof facing the supporting member 16. When screw 35 is tightened, pressure is exerted on the end of spring 31 facing supporting member 16, and the detents 32 are biased in radial outward direction. If a force is applied upon the cap in the direction away from the acetabulum, which means towards the supporting member 16, the detents 32 will yield in radial inward direction so that male member 17 can slide farther towards supporting member 16. In this way it is very easy during implantation to set the length of telescopic arrangement 15 such that inner surface 13 of the cap 11 firmly abuts the femoral head. Coupling 30, however, also provides for automatically setting the length of the telescopic arrangement 15, if the patient should suffer a long-term atrophy of bone tissue.

If, on the contrary, there is a force is applied upon prosthesis 10 tending to displace cap 11 towards the acetabulum, i.e. away from supporting member 16, the detents 32 will lean against the contacting surfaces 37 in the corresponding groove of the profiles thereof. This will effectively prevent any unwanted increase in the longitudinal dimension of the telescopic arrangement 15. By loosening screw 35 the surgeon, if necessary, can easily release coupling 30 and can lengthen the telescopic arrangement, wherein in the embodiments of FIGS. 1 and 2 the detents will remain in the female member and can be removed by pressing in the direction of the holding plate.

Telescopic arrangement 15 is further provided with a flexible member 40 which, in the embodiment of FIG. 1, is connected with male member 17. Flexible member 40 is placed at a certain distance form inner surface 13 of cap 11, which distance is about 1 to 3 times, and preferably about 1.5 times, the inner radius of cap 11. Flexible member 40, optionally in cooperation with hinge 19, at least partially permits natural biomechanical movements of the head and of the neck of the femur. The flexible member can also be replaced by an appropriate joint. Either the flexible member 40 or an appropriate joint are safeguarded against rotational motion, which means that they are structured such that the male member 17 itself remains torsion-proof. Moreover, male member 17 and female member 18 preferably have at least along a part of their longitudinal dimensions a profiled cross-section, particularly a polygonal or elliptical cross-section. In the embodiment shown, male member 17 has a hexagonal outer perimeter in its area cooperating with female member 18, whereas female member 18 is provided with a complementary hexagonal inner perimeter. In view of the fact that male member 17 and female member 18 are prevented from relative rotation and that flexible member 40 is torsion-proof, cap 11, after surgical implantation of prosthesis 10, is safeguarded against rotation on the femoral head and against loosening when frequently exposed to loads. Such loosening would cause pain to the patient and necessitate a new operation.

Flexible member 40 or an appropriate joint can be defined amongst others by a torsion-proof spring, particularly a hardened spring, e. g. in the form of a coiled spring or a drill shaft. It is also possible to use as the flexible member 40 a torsion-proof spring joint or an elastic insert. For example, a plastic collar which is profiled along its perimeter, e. g. by knurling, may be used as an insert. The insert can also be moulded of wire mesh. The flexible member 40 also may be interconnected with cap-side telescopic member 17 to form a single piece. For this purpose the male member 17, for example, may be provided with a spiral groove or the like. At least in the area 41 of cap 11 the cap-side telescopic member 17 has a circular cross-section, thus preventing to the full or at least utmost possible extent the creation of any pain centers which would be prompted by a sharp-edged design. In the embodiment of FIG. 1 the cap-side telescopic member 17 substantially centrically projects from the inner surface 13 of cap 11.

Figure 2:
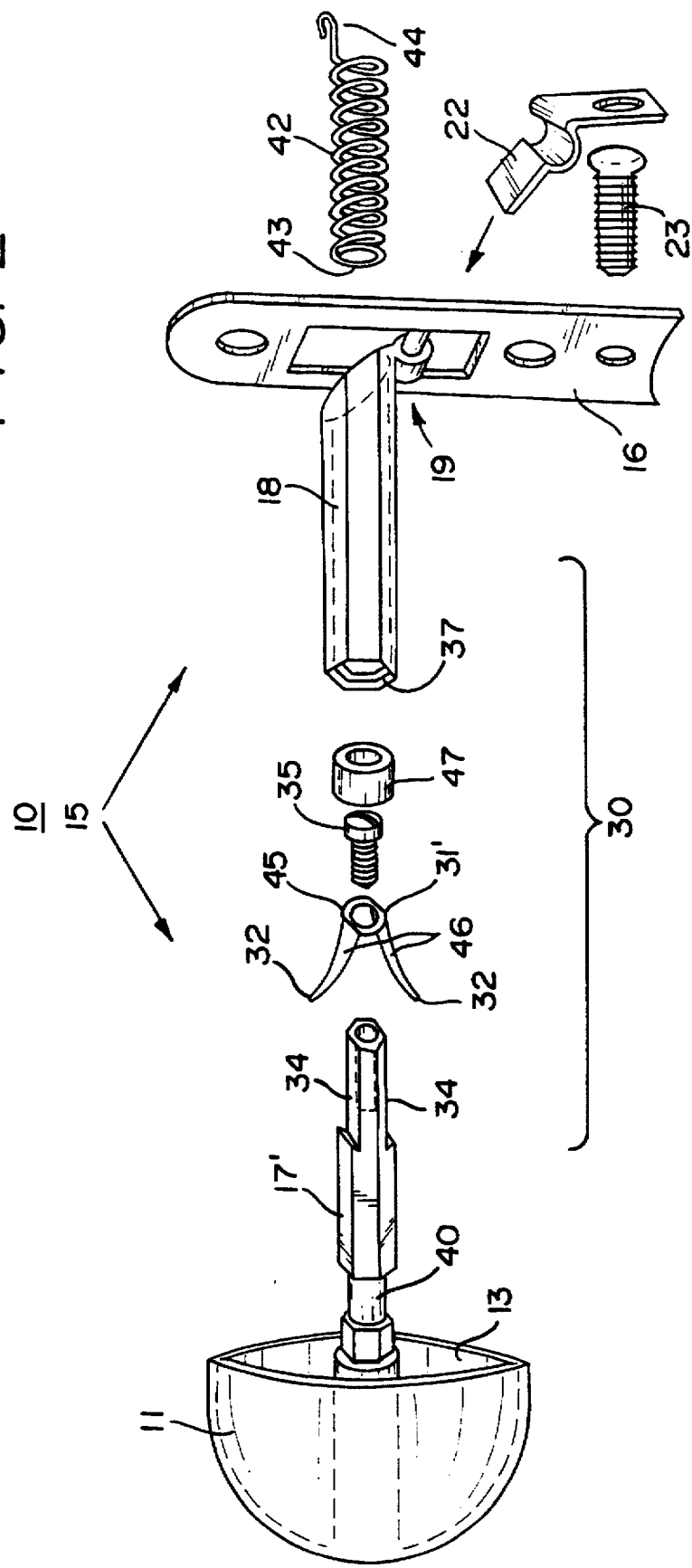
FIGS. 2 to 5 are views similar to FIG. 1 for modified embodiments of the prosthesis according to the invention.

In the modified embodiment of the prosthesis of FIG. 2 there is an additional tension spring 42 which biases the cap-side telescopic member 17' in the direction away from the acetabulum, that means towards the supporting plate 16. Tension spring 42 is disposed within the sleeve-shaped female member 18, and its end 43 facing the cap is connected to the cap-side telescopic member 17' by the screw 35. The opposite end 44 of tension spring 42 is attached to either the supporting member-side telescopic member 18 or to the supporting plate 16. The end 44 of the spring 42 is coupled for example to the outer edge of the female member. Instead of this, spring 42 could also be coupled to the transversal web 20. Instead of spring 31 made of bent wire there is spring 31' made of flat spring steel. Spring 31' has a circular base 45 from which spring arms 46 are bent off, these spring arms forming the detents 39 with their free ends.

To prevent during implantation an undesirable interference of detents 32 which might occur before the detents 32 engage the appropriate contact surfaces 37, a ring 47 may be used. Ring 47 is fitted over male member 17' to hold detents 32 down. When inserting male member 17' into female member 18, ring 47 will hit the free end of female member 18 and will be slid along female member 18 towards cap 11, thus releasing the detents 32.

In the embodiment of FIG. 2 a cap is used the edge of which runs in an oblique angle in relation to its longitudinal axis, whereas FIG. 1 shows a cap having an edge disposed in a plane which is perpendicular to the central longitudinal axis of the cap. It is obvious, that either the first or the second type of cap can be employed.

Figure 3:
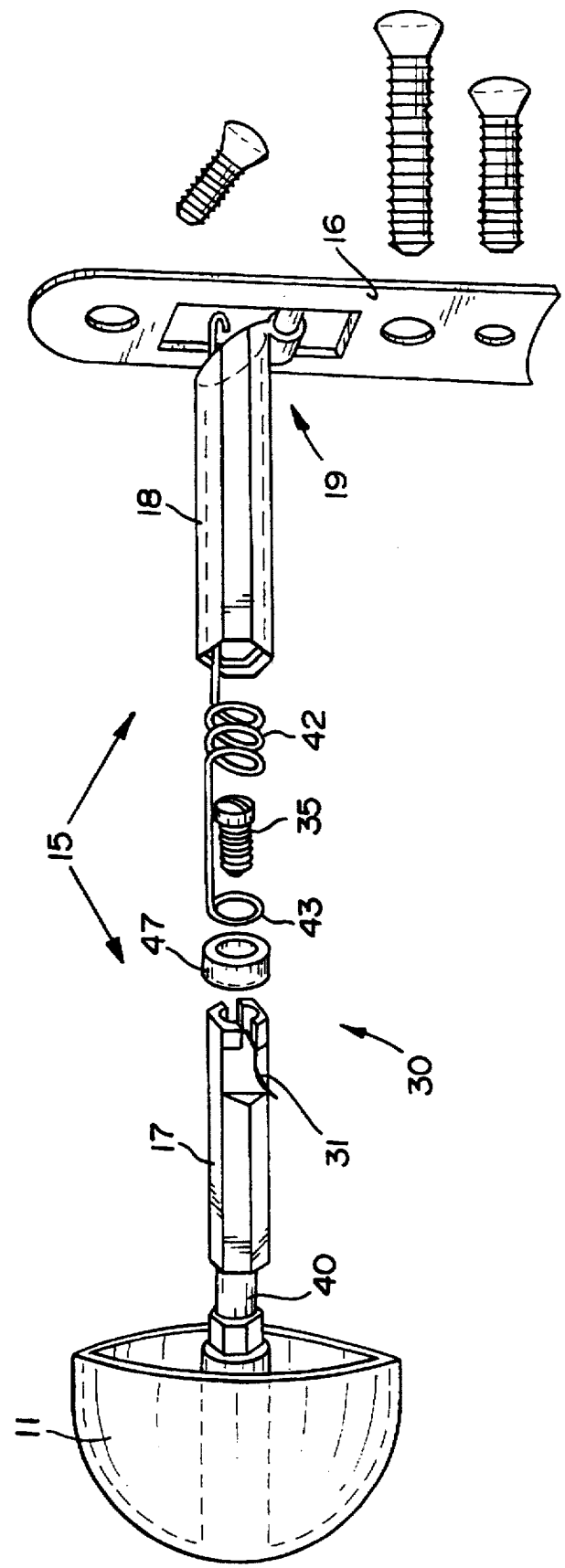

FIG. 3 represents an embodiment of the prosthesis which to a larger extent corresponds to the one of FIG. 2, but with the optional leaf spring 22 omitted, and spring 42 of FIG. 2 shown in its operational position.

Figure 4:
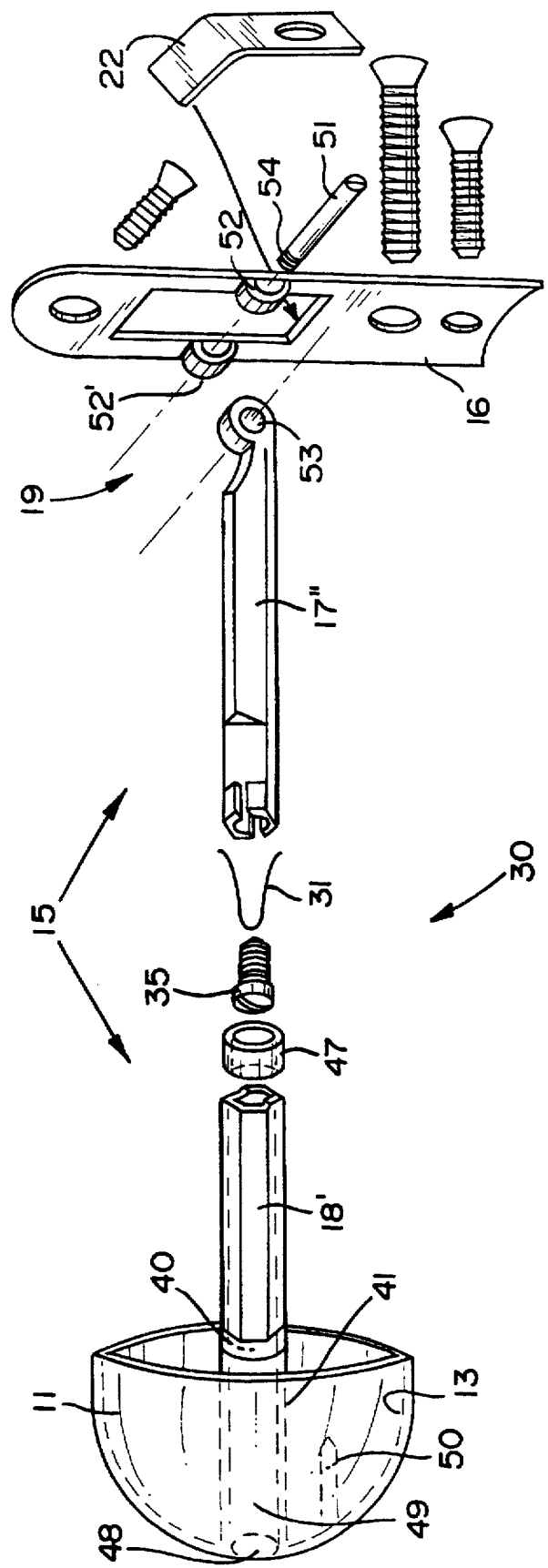

The embodiment of the prosthesis shown in FIG. 4 differs from the previously described embodiments mainly in that the supporting member-side telescopic member is a male member 17 and an associated female member 18' is attached to the cap. In accordance with the previously described embodiments the cap-side telescopic member 18' is of a circular cross-section at least in the area of the cap 41.

In this case, too, the flexible member 40 is disposed at a certain distance corresponding to one to three times the radius of the cap away from the inner surface 13 of the cap. Cap 11 is provided with a circular opening 48 coaxial to the longitudinal channel 49 of female member 18' to permit tightening or loosening of screw 35 as required. In this embodiment cap 11 is provided with an anti-twist member 50 which may be shaped like a sharp detent, spine, or the like, protruding from the inner surface 13 of cap 11 and eccentric and substantially parallel to the telescopic arrangement. It is to be understood that the anti-twist member may have varied shapes and sizes.

In this case the hinge 19 is provided with a pivot pin 51 which is held in two lateral eyes 52 and 52' of the supporting plate 16 and which extends through an opening 53 at the end of male member 17' facing the supporting member. Pivot pin 51 is provided at its one end with external threads 54 cooperating with corresponding inner threads of the eye 52'.

Figure 5:
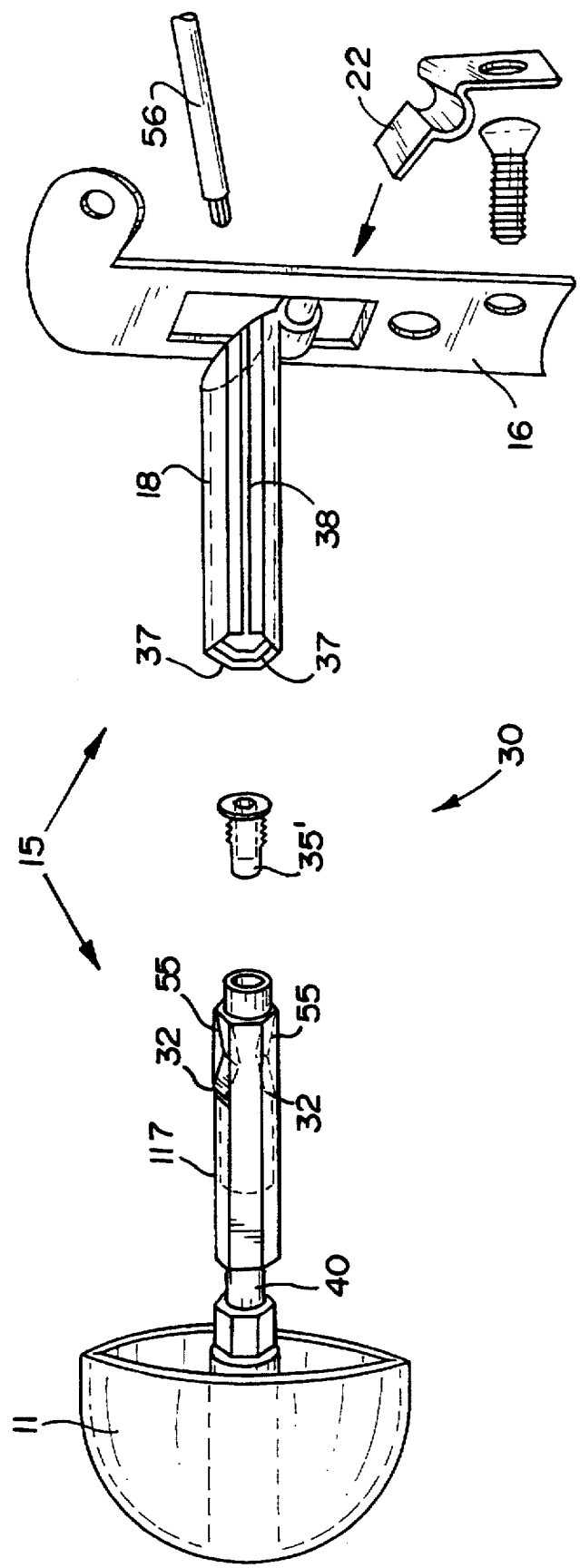

FIG. 5 illustrates another modified embodiment of the prosthesis in which the detents 32 are provided at the free ends of spring arms 55 which are fastened to a male member 117, e.g. by welding or soldering, or which are integrally connected to a part of male member 117, e. g. by being stamped out therefrom and bent out thereafter. As in the previously described embodiments, screw 35'—which, in this case, is shown as an inner-hexagon screw, is screwed into an internally threaded bore at the end of male member 117 facing female member 18 to bias the spring arms 55 in outward direction. Screw 35' can be set by a tool 56 which will be passed through the longitudinal channel of the female member 18. In the implanted state of the prosthesis screw 35' will take a position such that the detents 30 engage in recesses formed by the preferably saw-tooth shaped contacting surfaces 37 of the female member. If the telescopic arrangement is to be extended, screw 35' will be loosened, and the spring arms 55 return to their initial position in which they are disengaged from the contacting surfaces 37. In this embodiment the female member 18 is equipped with a longitudinal groove 38 which provides for the possibility of adjusting the size of the internal cross-section of the female member to comply with the size of the external cross-section of the male member 117 substantially without any clearance.

It is obvious that the restraining means can take on many different forms within the scope of the present invention.

Figure 6:
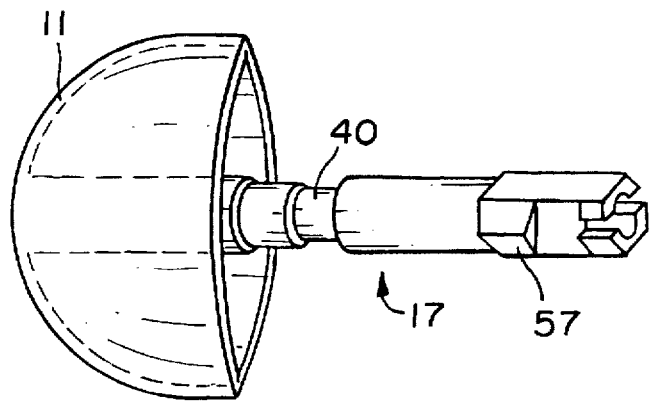
FIG. 6 is a perspective view of an insert member and a cap fixed thereto.
Figure 7:
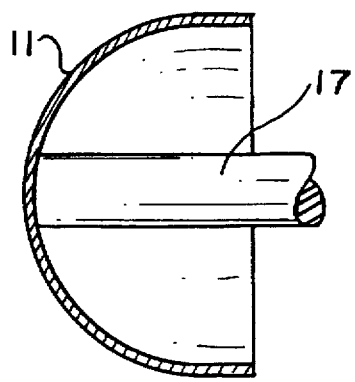
FIG. 7 is a sectional view of a cap and of a telescopic member eccentrically fixed thereto.

According to FIG. 6, portion 57 of male member 17 having a profiled, in the embodiment shown a hexagonal, cross-section, may be relatively short, and the remainder of male member 17 may be of circular cross-section. It is merely essential that the portion 57 with noncircular cross-section is long enough to prevent, in cooperation with the complementary female member, any relative rotary movements of the members defining the telescopic arrangement. FIG. 7 represents an embodiment where the telescopic member facing the cap, such as male member 17, extends at a predetermined distance from the central axis of the cap and parallel to this axis. This arrangement may, in itself or in addition to the described measures, provide for prevention of rotation of the cap 11 in relation to the head of the femur.

Figure 8:
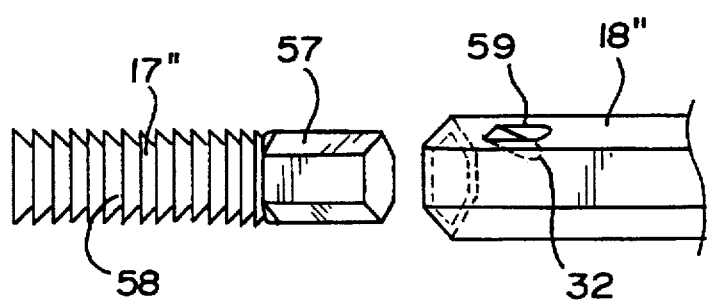
FIG. 8 is a perspective view of a modified embodiment of snap-in locking means for the telescopic arrangement.

FIG. 8 shows an embodiment of the telescopic arrangement where the profiled, for example hexagonal portion 57 of male member 17" is followed by a section 58 whose outer profile has a saw-like shape. A spring tongue 59 is stamped out of the wall of the female member 18" and bent inwardly. The free end of the tongue forms the detent 32 which, in the assembled state, will lockingly engage one of the latch grooves of section 58.

Optionally the male member and/or the female member of the telescopic arrangement may comprise two or more parts arranged one ahead of the other in the longitudinal direction of the telescopic arrangement with all of them being mutually locked against rotation or spontaneous release by being inserted into each other or by being screwed together.

Figure 9:
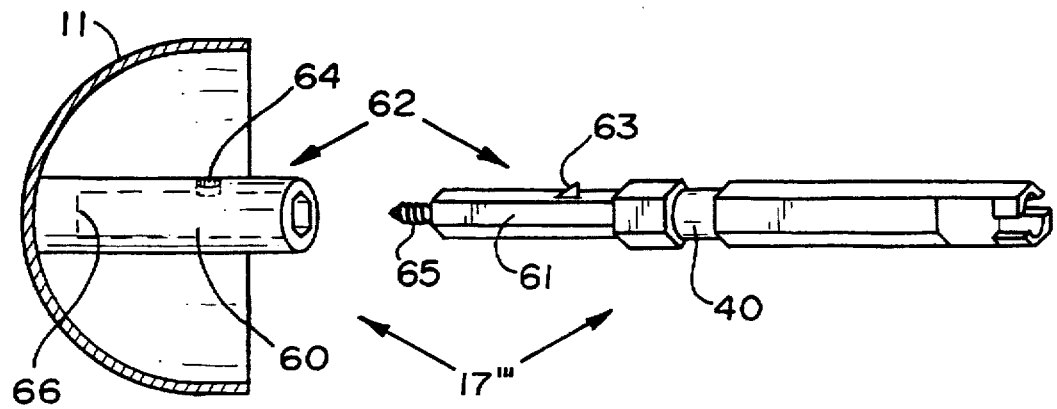
FIG. 9 shows an embodiment of a two-part male member, partially in sectional view and partly in perspective view.

FIG. 9 illustrates an example of a two-part male member 17''' consisting of two telescopic parts 60 and 61. Telescopic parts 60 and 61 have compleinentarily profiled (in this example hexagonal) cross-sections which, when the telescopic parts 60 and 61 are inserted into each other, provide for a torsion-proof interconnection. Parts 60 and 61 of male member 17''' can be mutually connected by snap-in locking or latch means 62. Means 62 can be designed in many different ways, e.g. in the same manner as coupling 30 provided for the interconnection of male member 17 and female member 18. In the embodiment of FIG. 9 one or more, preferably saw tooth-shaped, latching detents or noses 63 are provided which project from the telescopic part 61 in radial outward direction and which engage in one or more of the recesses 64 of the telescopic part 60. A spring 65 fixed to the front end of telescopic part 61 and acting in the longitudinal direction of male part 17 leans against the bottom 66 of the bore in telescopic part 60, thus providing for safe, clearance-free coupling of mutually interlocked parts 60 and 61 upon the latching detents or noses 63 being engaged in the recess 64.

Figure 10:
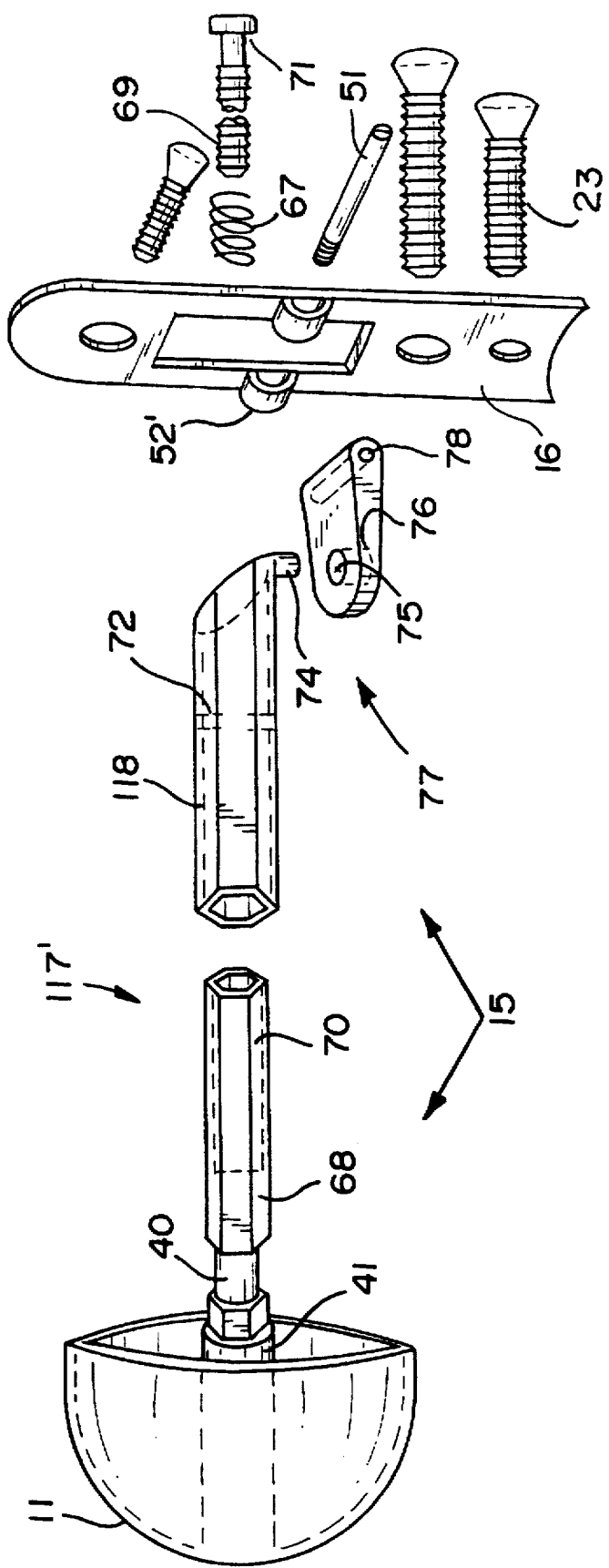
FIG. 10 is a perspective exploded view of a further embodiment of the prosthesis according to the invention.

In the further alternative embodiment of the prosthesis shown in FIG. 10 the direction-dependent restraining means which permits displacement of cap 11 relative to the fixation plate 16 in the direction towards the fixation plate 16, but impedes displacement of cap 11 relative to the fixation plate 16 in the direction away from the fixation plate 16, is defined by spring biasing means including a biasing spring 67. In this embodiment male member 117' comprises a part 68 connected with the cap 11, as well as another equiaxed part 69, which parts 68, 69 are detachably interconnected. In the embodiment shown, part 69 is formed by a screw which is screwed into an internally threaded bore 70 of part 68. Part 69 includes an external shoulder 71 against which biasing spring 67 leans with its right-hand end in FIG. 10. The opposite, in FIG. 10 the left, end of biasing spring 67, which is designed as a compression spring, leans against an internal shoulder 72 of female member 11 when the prosthesis is in the assembled state. The force exerted by the biasing spring 67 draws male member 117' together with cap 11 in the direction towards the supporting plate 16. In the same manner as in previously described embodiments the telescopic arrangement will thus automatically adjust its length to given circumstances prevailing at the site of implantation, even if after implantation there occurs bone resorption or the like.

Female member 118 has at its end facing the supporting plate 16 a pivot pin 74 which is rotatably fitted into an opening 75 of a pivot plate 76. Pin 74 and opening 75 cooperate to form a hinge 77 the axis of rotation of which is substantially perpendicular to the longitudinal axis of the telescopic arrangement, and substantially parallel to the longitudinal extension of the supporting plate 16. When in the assembled state, pin 51 extends through another opening 78 of pivot plate 76, wherein the axis of opening 78 is perpendicular to the longitudinal axis of the telescopic arrangement.

In the case of above embodiments the hinged coupling between the telescopic arrangement and the fixation plate will ensure that the prosthesis will retain its dynamic features after implantation in the femur bone, so that the prosthesis will transmit pressing, tractive and shear forces and will direct them into the head and neck of the femur in an approximately natural manner. A further advantage of the pivotal connection between the telescopic arrangement and the supporting member rests in a much easier handling of the prosthesis during the surgical intervention, in particular when it is being fitted to the surface of the lateral femur bone. In this way a large-surface contact between the supporting plate 16 and the surface of the lateral femur bone is possible independently of the angle between the central longitudinal axis of the femur bone and the bore receiving the telescopic arrangement.

Figure 11:
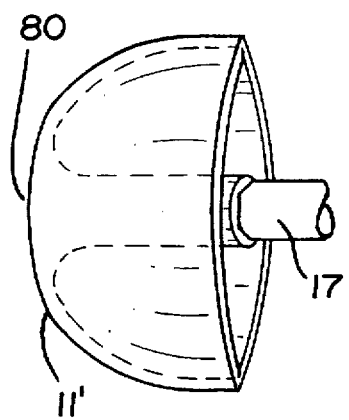
FIGS. 11 to 13 are perspective views of various types of caps.

The cap 11' represented in FIG. 11 is flattened in the region of its pole area 80. Furthermore the cap may be optionally thickened in outward direction in the edge area of the cap. By using such measures it may be possible, dependent on the state of the natural acetabulum, to implant a cap prosthesis avoiding protrusio acetabile without employing an artificial acetabulum.

Figure 12:
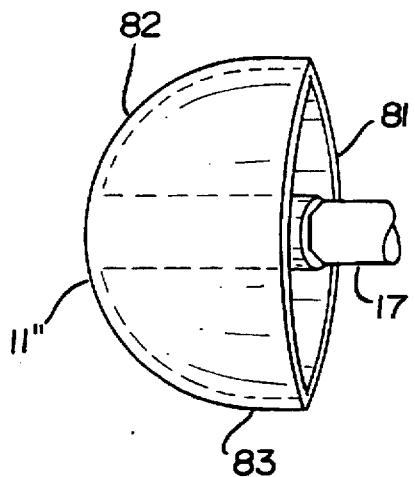

As it follows of FIG. 12, the edge 81 of the cap 11, at least for a major part thereof, lies in a plane which is oblique-angled with respect to the longitudinal axis of the telescopic arrangement such that, in the implanted state, it will cover the head of the femur at least close to evenly. It also can be seen that a more or less cylindrical cap part 83 follows the at least approximately semi-spherical part 82 of the cap.

Figure 13:
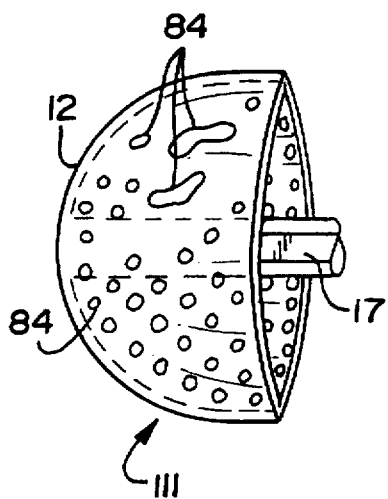

FIG. 13 represents a sieve-shaped cap 111 having a large number of recesses or openings 84 to reduce the contact surfaces and thus lower mechanical wear and generation of heat between the cap and the acetabulum. The head of the femur is supplied through openings 84 with joint fluid with particular effectiveness. For the purpose of reducing wear of the acetabulum, the openings 84 are deburred at the outer surface of the cap or are cone-shaped.

Figure 14:
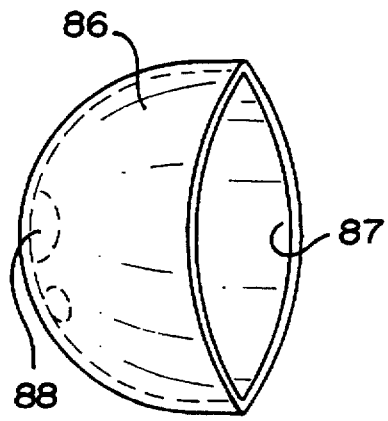
FIG. 14 is a perspective view of a cap insert.

FIG. 14 shows an insert 86 which optionally can be used as an internal part of cap 11 and may be inserted into the cap, wherein the inner surface 87 of the insert is at least approximately adapted to the shape of the prepared or unprepared head of the femur. The insert 86 is selected from a group of inserts differing in wall thickness or in shape and inserted into the cap to adapt the internal diameter and internal shape of the cap to the diameter and shape of the particular femoral head. In this way an almost precise, clearance-free fitting of the cap to the femur head can be ensured. The insert 86 is provided with a central opening 88 through which, in an assembled state, the cap-side telescopic member will extend. The insert 86 e.g. may be made of polyethylene.

Figure 15:
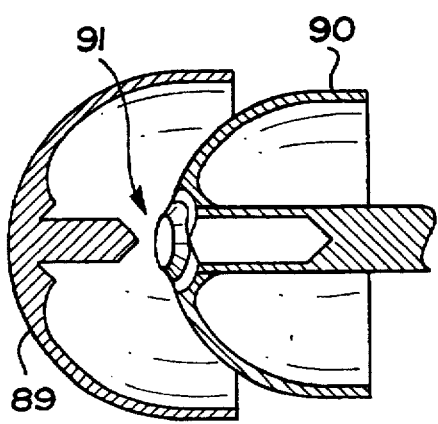
FIG. 15 is a sectional view of a two-part cap.

In accordance with the FIG. 15 the cap, for example cap 11, may consist of two parts wherein a tray-shaped upper part 89 contacts with its internal surface the outer surface of a tray-shaped lower part 90. The upper part 89 and the lower part 90 may be mutually supported by a bearing 91. Bearing 91 may be for example of needle type in conic arrangement.

Figure 16:
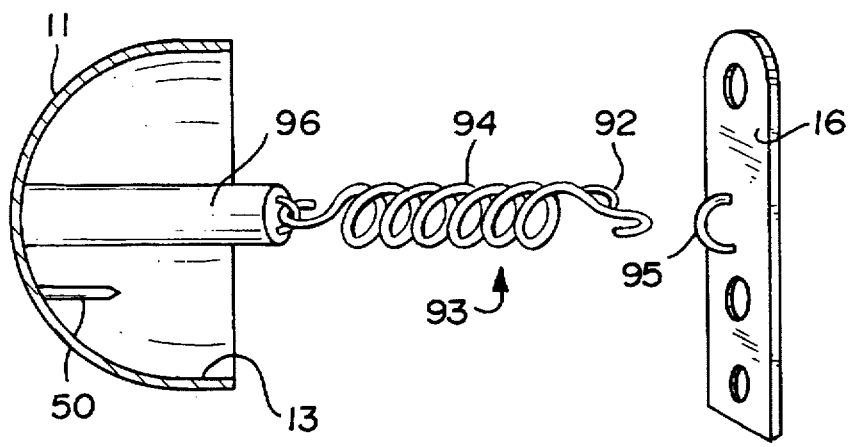
FIG. 16 shows a simplified embodiment of the prosthesis partially in section, partially in perspective.

The prosthesis 10 of FIG. 16 represents a simplified embodiment without a telescopic arrangement. It comprises restraining means 93 which impedes relative displacement between cap 11 and supporting plate 16 in the direction away from supporting plate 16 more than in the direction towards the supporting plate. Restraining means 93 consists of at least one tension spring member 94 which is shown in FIG. 16 hung with its right end in an eye 95 of supporting plate 16. The other end of tension member 94 is connected with a stem 96 projecting from internal surface 13 of cap 11. During implantation this tension member may be gripped with a tool at an eye 92 and stretched out to be hung to eye 95. To be secured against rotary motion, cap 11 has at least one member 50 providing for security against rotation. Apart from this or in addition thereto the stem here like in the case of the other embodiments may have an eccentric position in respect to the cap (FIG. 7).

Figure 17:
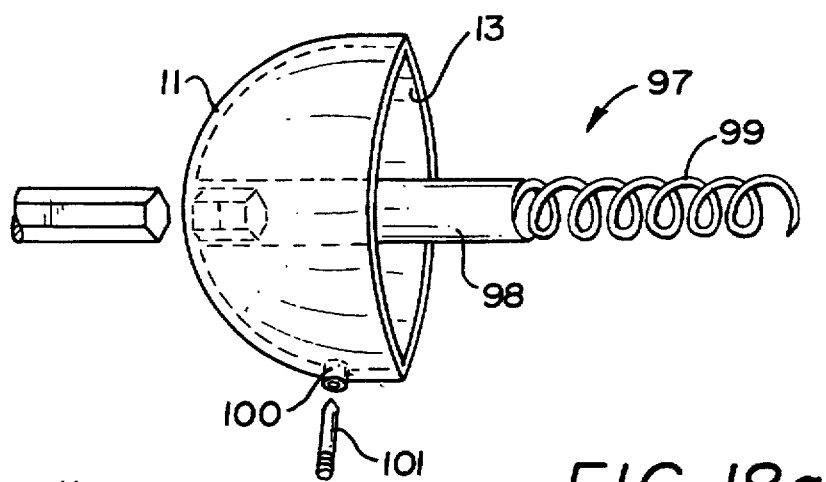
FIGS. 17 and 18a are perspective views of two additional modified embodiments of the prosthesis in accordance with the invention.

FIGS. 17 and 18 show further altered embodiments of the joint prosthesis. They have in common that the stem, which projects from cap 11, is itself designed as an anchoring member. In the case of the embodiment depicted in FIG. 17 a stem 97 is provided which includes a cylindrical part 98 connected with cap 11 as well as an adjoining part 99 having the shape of a corkscrew. Stem 97 has a centric position in respect to cap 11, and its corkscrew-shaped part can be screwed into a bore and bone tissue, wherein the stem 97 is guided within the bore made in the head of the femur and adjacent parts of the bone. Cap 11 is equipped with at least one eccentric recess 100 into which an anti-twist or rotation blocking member 101 can be introduced from outside into the femoral head. Rotation blocking member 101 e.g. may be a spike which is driven into bone tissue through recess 100. Rotation blocking member 101, however, also may be fitted with external threads engaging internal threads of recess 100 to be screwed into the bone tissue. Preferably, the rotation blocking member 101 is countersunk in cap 11.

Figure 18A:
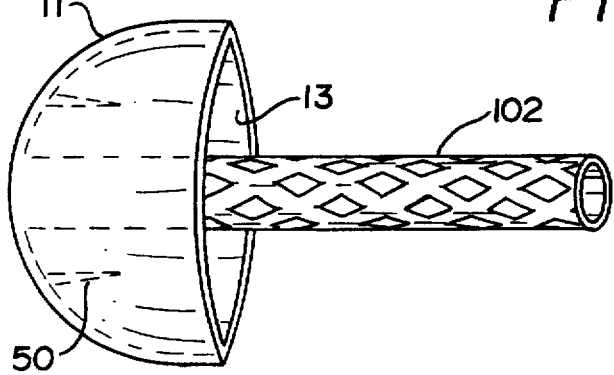

In the case of the further embodiment of FIG. 18a there is a stem 102 having at least along a part of its longitudinal dimension the form of a sleeve provided with a grid-shaped wall. After implantation bone tissue can grow into the grid. The stem 102, however, may also be designed at least in part as a pin having an overall porous structure or at least a porous structure at the outer surface thereof. Stem 102 shown in FIG. 18a has a centric position in relation to the cap; it is obvious that instead of this, stem 102 may be eccentrically disposed to prevent rotation of the cap.

Members 50 for preventing rotation project from the inner surface of tile cap, in parallel to stem 102. It is obvious that instead of this, either one or more of the anti-rotation members 101 of FIG. 17 may be employed, or that the prosthesis of FIG. 17 may be provided with at least one of the anti-rotation members 50.

The various parts of the joint prosthesis can be made of any suitable materials, in particular stainless metal, like high-grade steel, titanium, chromium, or the like, and/or alloys of the above metals and/or plastic materials, such as polyethylene, and/or ceramic materials, or combinations of such materials.

The contacting surfaces for the one or more detents also can be made without any profile, or may be provided with a coating into which the detent(s) can dig in. In the case of the prostheses according to FIGS. 1 to 16 an additional sleeve can be used (not shown here) which can be inserted into the bore and which, in the implanted state, surrounds the telescopic arrangement or the tension member or the stem for at least a part of the longitudinal dimension thereof. Such a sleeve, made of plastic material, can prevent the metal parts of the prosthesis from contacting natural tissue. Instead of this, or in addition thereto, the metal parts of the prosthesis may be provided with a non-metallic coating, particularly a plastic coating. A rigid sleeve, e.g. a metallic sleeve, may be used, if necessary, to stiffen the flexible member 40. Such a stiffening also can be reached for example by providing a female member of sufficient length to extend over a flexible member disposed in the male member of the telescopic arrangement. In the case of the embodiments shown the telescopic members are prevented from relative rotation by an appropriate shape of the cross-sections thereof. The members of the telescopic arrangement, however, may also have a circular cross-section, particularly if a rotation of the cap on the femoral head is prevented by any other convenient means like e.g. an eccentric arrangement of the cap-side telescopic member, by making use of at least one spike preventing such rotation, or the like.

Figure 18B:
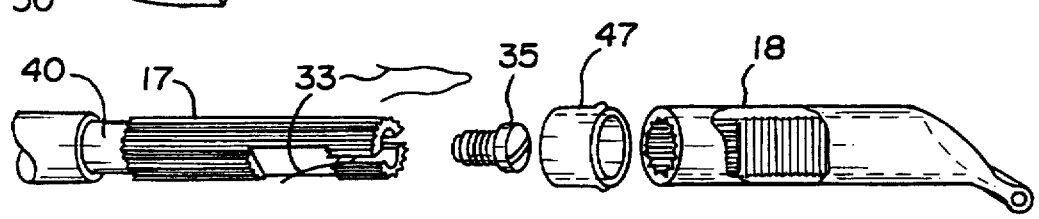
FIG. 18b is a partial perspective view of a telescopic arrangement in which the telescopic members are engaged with each other via a serration.

In the embodiment of FIG. 18b the male member 17 comprises external splines which engage internal splines provided in a hub at the facing end of female member 18, thus preventing any rotation between the male and female members. The internally splined hub is followed in axial direction by the saw-like profile described in detail above, e.g. with reference to FIG. 1.

Figure 19:
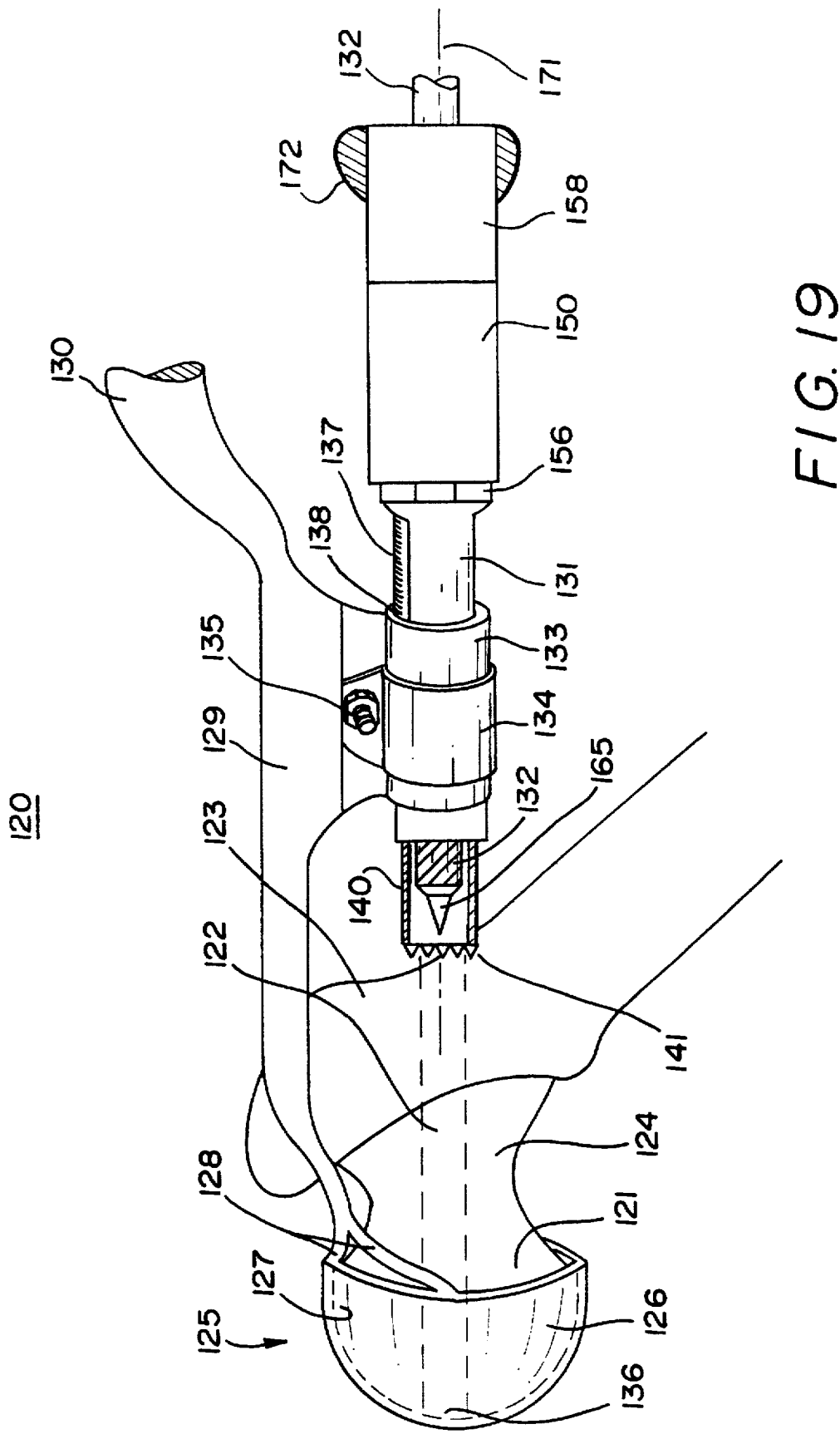
FIG. 19 is a perspective partially broken view of a surgical device for forming a drilling.

FIG. 19 represents an example of a surgical device 120 designed for making a precise, prior scheduled drilling 122 in the given axis, concentric in respect to the femur head indicated at 121 from the side of the femur shaft, i.e. through the femur shaft 123, the neck 124 of the femur and femoral head 121. The device 120 comprises receiving means 125 including a receiving member 126 shaped like a spherical cap and designed for at least partially receiving the femur head 121. The receiving member 126 can be set onto the femur head 121 as it is shown in FIG. 19, and the inner shape thereof is adapted to the outer shape of the femur head such that the inner surface 127 of the receiving member 126 can at least partially abut the outer surface of the femur head. The receiving member 126 is connected by means of holding webs 128 to a lateral holder 129 fitted with a handle 130 or the like at its end opposite to the receiving means 125.

Figure 44:
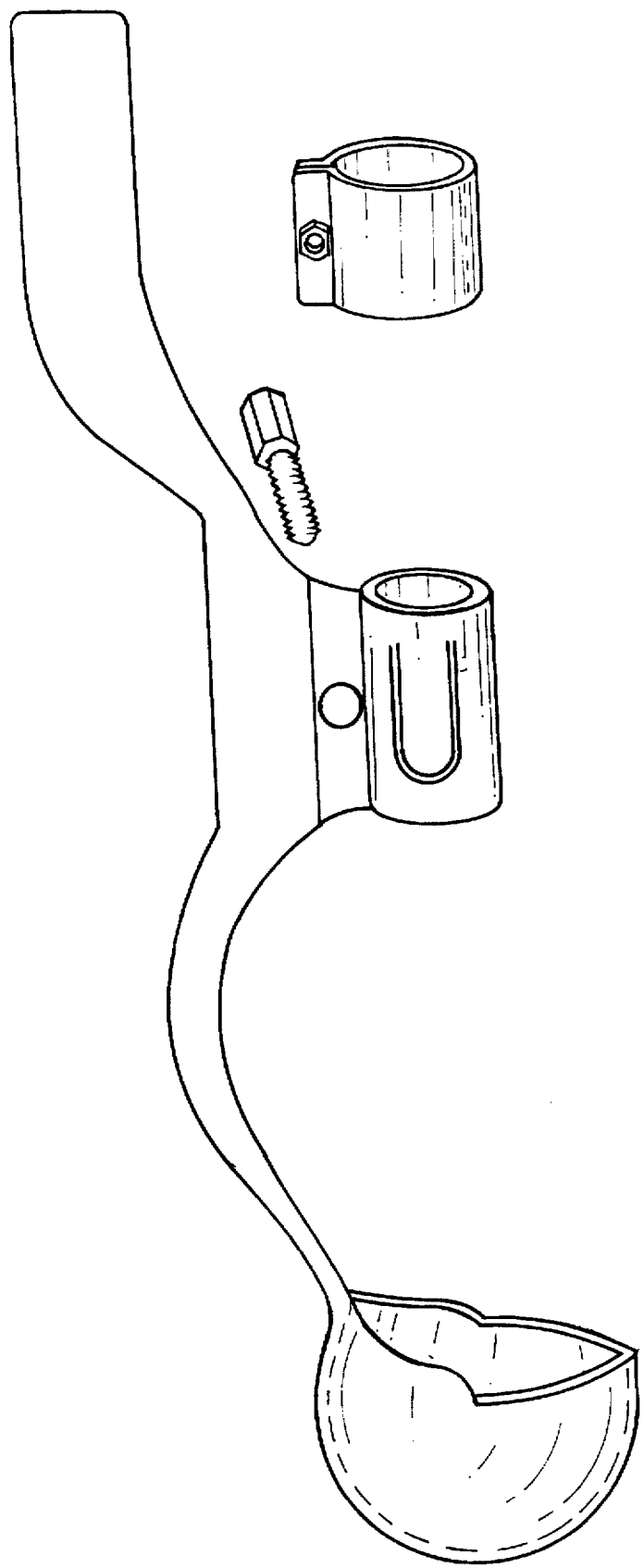
FIGS. 44 and 45 are schematic partial views of further modified embodiments of the device for forming drillings in accordance with the invention.
Figure 45:
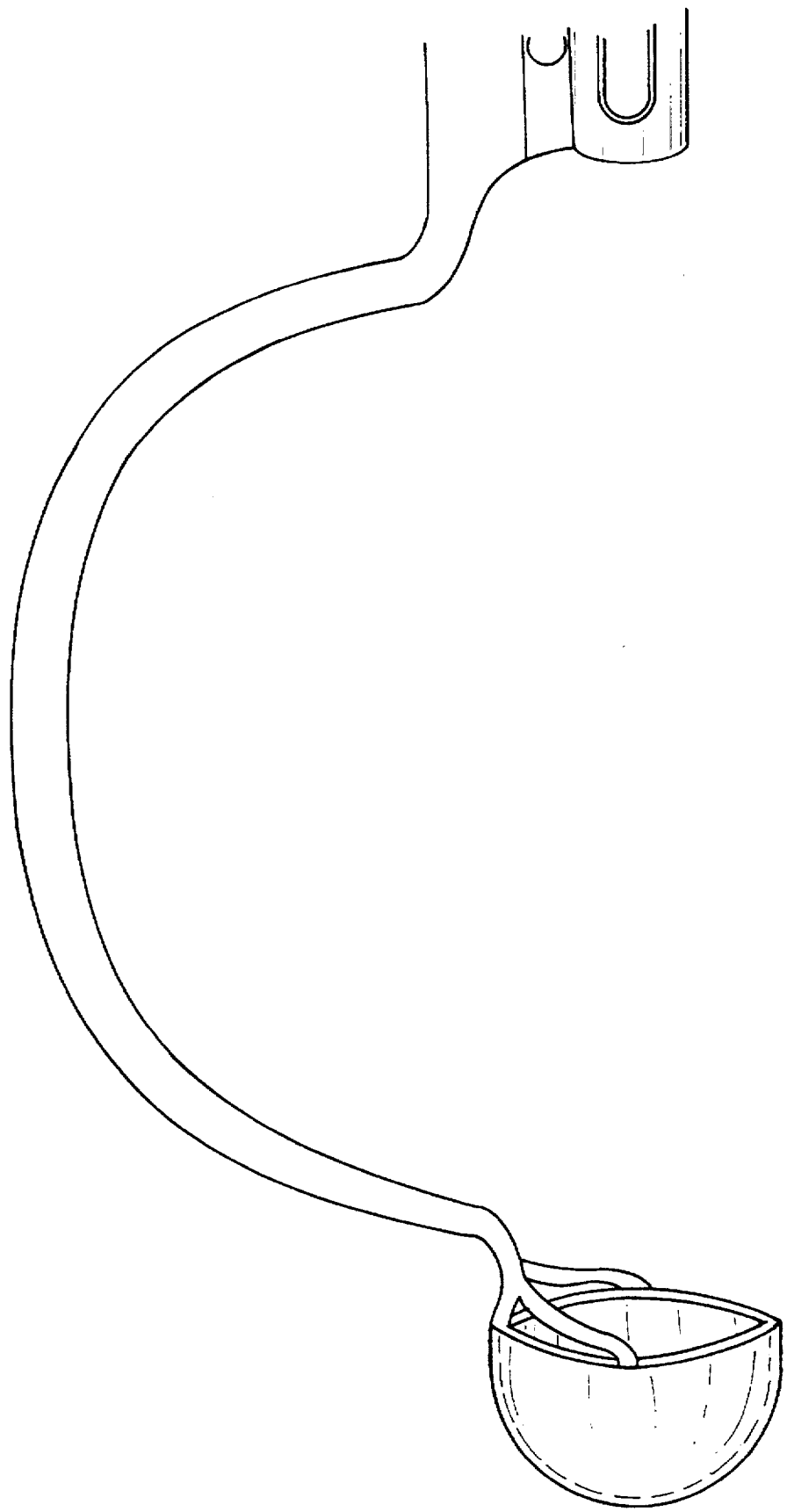

The holding webs 128 are bent such that after putting the receiving member 126 over the femur head 121 the femur head, which beforehand has been dislocated from the femur joint socket, can be repositioned. To obtain a larger clearance the holder 129 can moreover have the shape of an arch in its part facing the cap, as it is shown in FIG. 44. In accordance with FIG. 45 there can be a rather big arch allowing for making a drilling with use of a medial access as well as a lateral cut, where the arch lies in front of the femur.

The lateral holder 129 is further attached to a receiving sleeve 131 for receiving a drill 132 or an other instrument. In the illustrated embodiment the receiving sleeve 131 extends through a pipe socket 133 fixed to the holder 129. The pipe socket 133 has associated thereto a pipe clamp 134 which can be either tightened or loosened, as required, by a screw 135. The receiving member 126 is located in the longitudinal central axis of the receiving sleeve 131. On having loosened screw 135 the receiving sleeve 131 can be repositioned along its longitudinal axis relative to the receiving means 125. The axial distance between the front end of the receiving sleeve 131 and the plummeting point 136 of the central longitudinal axis of the receiving member 126 on the inner surface 127 thereof can be read e.g. from a scale 137 which is located on the outer surface of the receiving sleeve 131 and which cooperates with the rear edge 138 of the pipe socket 133 for indicating the distance. By tightening the screw 135 and thus also the pipe clamp 134 the receiving sleeve 131 can be locked relative to the holder 129 and the receiving member 126. As it is obvious from FIGS. 19 and 20 there is an intermediate sleeve 140 which in radial direction is disposed between the receiving sleeve 131 and drill 132 and which extends coaxially to the latter. The intermediate sleeve 140 axially projects beyond the receiving sleeve 140 at both ends thereof. At the end facing the receiving means 125 the intermediate sleeve 140 is fitted with a crown 141 of spikes or the like. Instead of this crown 141 of spikes other sharp pointed protrusions or the like can be provided on the intermediate sleeve 140.

In order to be able to firmly clamp the femur head 121 in the receiving means 125 and thus to relatively tightly fix the device 120 and the femur shaft and femur head, the intermediate sleeve 140 is mounted in the receiving sleeve so that it may be moved along the longitudinal axis, but is prevented from relative rotation. For preventing relative rotation a groove and tongue system is provided in the illustrated embodiment, which system includes a tongue 142 which protrudes from the inner surface of the receiving sleeve 131 in inward radial direction and which is guided for longitudinal sliding movement in a slot or groove 143 of the intermediate sleeve 140. The intermediate sleeve 140 is fitted at its end opposite to the crown 141 of spikes with an external thread 144 which is in threaded engagement with an internal thread 145 of a repositioning sleeve 146. The repositioning sleeve 146 is provided at its end averted from the receiving means 125 with an actuating member 147 which in the illustrated example is designed as a sleeve section with the hexagonal cross-section.

When in assembled state, the front surface 148 of the repositioning sleeve 146, which faces the crown 141 of spikes, abuts the face 149 of receiving sleeve 131 remote from the receiving means 125. The repositioning sleeve 146 is held in this position by a fixation sleeve 150 which is screwed by means of an internal thread 151 onto an external thread 152 on the end of the receiving sleeve 131 averted from the receiving means 125. The fixation sleeve 150 has an internal stop, preferably in the form of an internal shoulder 153, which will contact an external stop of the repositioning sleeve 146 having in the illustrated example the form of an external shoulder 154. In this way the repositioning sleeve 146 is mounted so as to be rotatable in relation to the receiving sleeve 131 and fixation sleeve 150 but to be fixed in its axial position. The fixation sleeve 150 can be locked in relation to the receiving sleeve 131 by pressing its end 155 facing the receiving means 125 against a web 156 by tightening the threads 151, 152, wherein web 156 is protruding from the outer side of the receiving sleeve 131 and is limiting the externally threaded section 152 in the direction towards receiving means 125. As indicated in FIG. 19 the perimeter of web 156 can be provided with flattened surfaces allowing for safe grasp of the receiving sleeve 131 with a tool during tightening of the fixation sleeve 150.

Figure 20:
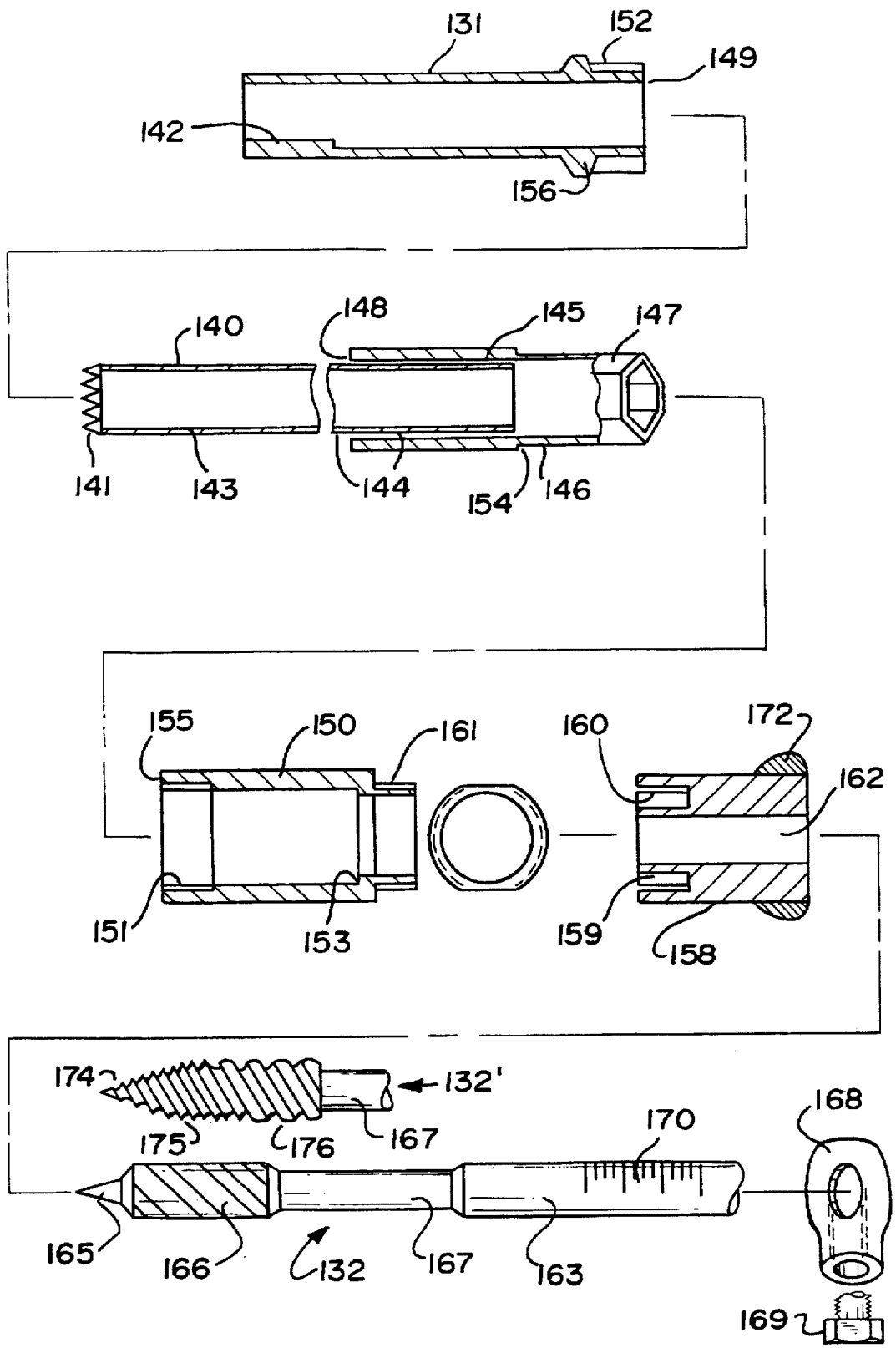
FIG. 20 is an exploded sectional view of a part of the device of FIG. 19 in connection with two different embodiments of the drill.

The fixation sleeve 150 is releasibly connected with a centering sleeve 158. In the embodiment of FIGS. 19 and 20 the centering sleeve 158 is provided for this purpose in the area of an axial groove 159 with an inner thread 160 which cooperates with an outer thread 161 of the fixation sleeve 150. The centering sleeve 158 is provided with a longitudinally extending bore 162 having an internal diameter which is adapted to the outer diameter of a shank 163 of drill 132 or of another instrument such that the shank will be received substantially without any clearance. Herewith a precise guidance of the drill 132 is ensured when it is penetrating into the bone system.

The drill 132 illustrated in FIG. 20 has a centering drill tip 165 followed by a blade 166. A section 167 of the drill 132 lying in longitudinal direction between the blade 166 and shank 163 has smaller diameter than blade 166. Herewith the frictional heat generated in the course of drilling is maintained at a low level. Apart from that, the annular space left between the circumferential surface of section 167 and the internal wall of the intermediate sleeve 140 catches the borings generated during the process of making the drilling 122. A stop 168 may be provided on shank 163 of the drill, which stop is fixed to the drill 132 by a screw 169. The shank 163 of the drill is fitted with a longitudinal scale 170. By appropriate setting the stop 168 relative to the longitudinal scale 170 the depth of drilling can be determined, for example such that the centering drill tip 165 will be at a small distance in front of the plummeting point 136 when the stop 168 hits the centering sleeve 158.

On the basis of X-ray pictures taken before the surgical intervention the device 120 can be preset with use of the longitudinal scales 137 and 170. By loosening and again tightening pipe clamp 131 and screw 135, the receiving sleeve 131 is brought into a suitable distance from the receiving member 126, and the depth of drilling is set by positioning the stop 168 along the drill shank 163. The intermediate sleeve 140 is pushed back inside the receiving sleeve 131 and does not or only slightly protrude from the end of the receiving sleeve 131 facing the receiving means 125. Thereafter the receiving member 126 is put onto the prepared on unprepared femur head 121 in the manner indicated in FIG. 19 whereby the central longitudinal axis 171 of the receiving sleeve 131 and thus also the longitudinal axis of the drill will be automatically centrically aligned relative to the femur head 121. Then the repositioning sleeve 146 is to be turned by a suitable tool, such as a wrench with the inner hexagon inserted into the actuating member 147, in order to move the intermediate sleeve 140 towards the receiving member 126 by means of the engagement of threads 144 and 145 until the crown 141 of spikes becomes firmly engaged with the femur shaft 123. The threads 144, 145 preferably are left-handed threads. The device 120 will thus be securely fixed to the bone system. Now the centering sleeve 158 is screwed to the fixation sleeve 150, and the drill is advanced, with the adjusted depth of drilling, until its point touches the bone. Then the drill 132 is rotated by a suitable power source, like a pneumatic drive, and is moved towards the receiving member 126 until the stop 168 hits the centering sleeve 158. By interaction of the drill shank 163 and centering sleeve 158 the drill is precisely guided, whilst the generation of frictional heat in the drilling channel is kept at a low level due to the section 157 of reduced diameter. When using a tool with different outer diameter, the centering sleeve 158 can be replaced by a centering sleeve having a correspondingly adapted bore diameter. Such a replacement is facilitated by handles or projections 172 on the centering sleeve (FIG. 20).

FIG. 20 shows at 132' a modified embodiment of the drill provided at the tip thereof with a conical cutting section 174 which is followed by a short threaded section 175 which in turn is followed by a main cutting section 176. The main cutting section 176 has again as its continuation a section 167 of reduced diameter. The threaded section 175 provides for advancing of the drill 132' within the bore channel, so that the drive means for the drill essentially only has provide for the power to rotate it.

FIG. 21 is an exploded view of sleeve 133, pipe clamp 134 and screw 135. When the parts are assembled, screw 135 passes through aligned bores 177 and 178 of holder 129 and pipe clamp 134, respectively, and the screw is threaded into a nut 179 fixed to a leg 180 of pipe clamp 134. In order to transmit the clamping force acting on receiving sleeve 131, two spring tongues 181 are formed at diametrically opposite sides of the pipe socket 133. Instead of this or in addition thereto the pipe socket 131 may be provided for example with a through-passing longitudinal slot 182, as it is shown in FIG. 23.

In the embodiment of FIG. 24 the receiving member 126 is formed by a flat strap 184 the internal shape of which likewise is adjusted to fit the outer shape of the femur head 121 such that its inner surface can be contacted with at least a part of the outer surface of either the prepared or unprepared femur head. The width of the flat strap 184 can vary within a wide range. It must only be ensured that on putting the internal surface of the flat strap 184 on the outer surface of the femur head the central longitudinal axis of the receiving sleeve 131 must precisely aligned in relation to the joint head periphery and the device 120 must be correspondingly positioned relative to the bone system.

In the further modified embodiment of the receiving means 125 according to FIG. 25 a for example annular holding means 185 is attached to the holder 129, which holding means may be releasibly connected to the receiving member 126. The receiving member 126 is shown in FIG. 25 as a cap. Instead of this, however, e.g. a flat strap corresponding to the flat strap 184 as shown in FIG. 24 may be used. The receiving member 126 may have various sizes to fit the size of the femur head, and it can abut with outwardly directed protrusions 186 or e.g. a ring-shaped web a supporting surface 187 of the holding means 185. The receiving member 126 can be releasibly fixed in the holder 185 with help of fixing means not illustrated in detail. As a fixation A latch, snap in or similar type of mechanism e.g. may be used, as well as a screw coupling between the outer surface 188 of the receiving member 126 and the internal circumferential surface and/or the supporting surface 187 of the holding means 185.

Figure 26:
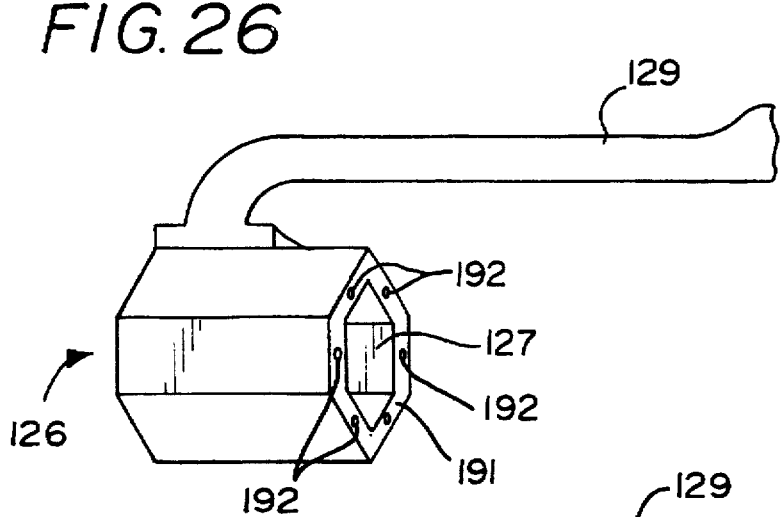
Figure 27:
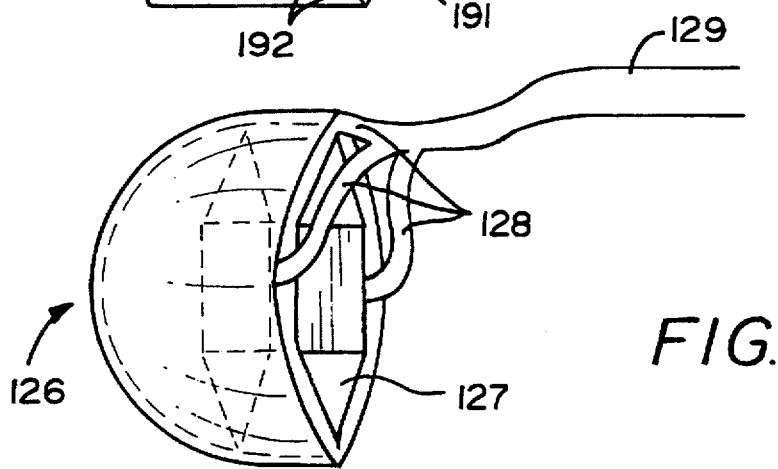

The embodiments of the receiving members 126 depicted in FIGS. 26 and 27 are provided with an internal space of hexagonal cross-section, wherein the receiving member 126 of FIG. 26 is formed by a sleeve and the receiving member 126 of FIG. 27 is formed by a cap. Such a receiving member will contact the respective joint head at three or more points of its internal surface 127 and/or of its front surface 191, for example at three or more points of front surface 191 which, as represented in FIG. 26, define bearing points 192 arranged in this case in a single plane. It is to be understood that the receiving member 126 can also be formed by an otherwise shaped body, like a triangular, quadrangular or other polygonal body. A precise positioning and adjustment of the joint head relative to the central longitudinal axis of the receiving sleeve 131 is guaranteed by at least three contact points 192 of the receiving member 126 which will interact with the periphery of the femoral head. Basically, hollow cylinders and hollow cones or otherwise shaped bodies are also adapted to be used as receiving member, if they will at least partially receive the femoral head and if they are adapted to contact its outer surface or its periphery at at least three trigonally arranged points.

Figure 28:
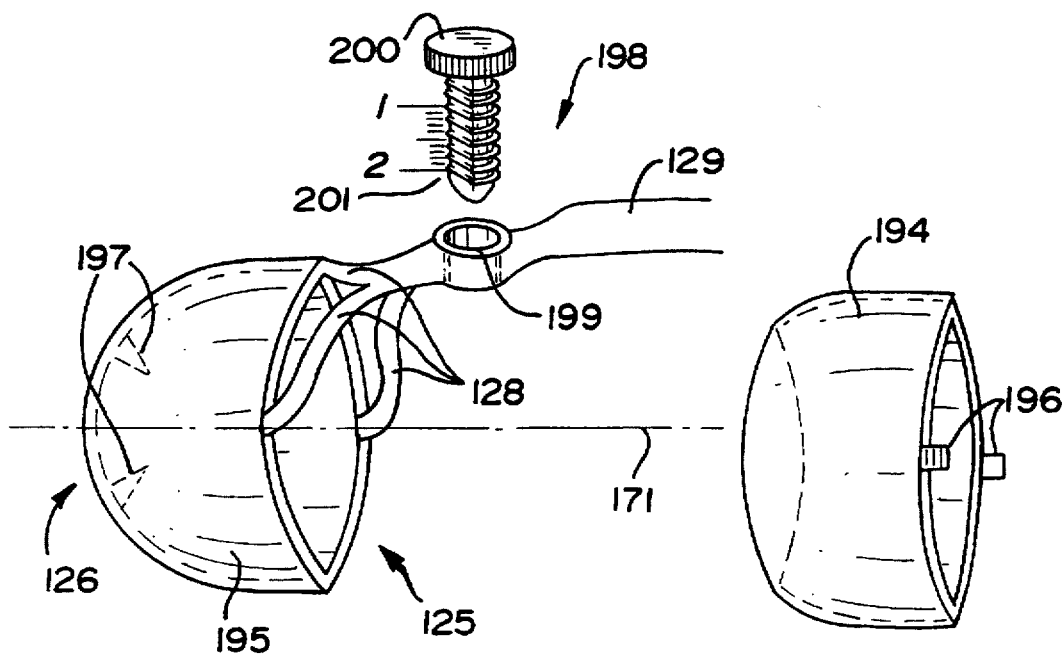
FIG. 28 shows a further modified embodiment of the receiving means in connection with adjusting means and an insert member for the receiving member.

FIG. 28 shows another embodiment of the receiving means 125 where an insert 194 is provided as a part of the receiving member 126 and/or of the receiving means 125, which insert can be selected from a group of inserts differing in their wall thickness and/or in their internal shape to adapt the internal diameter and/or the internal shape of the receiving member to the given diameter and/or the outer shape of the joint head, and is detachably and exchangably inserted into a part 195 of the receiving member fixedly connected to the holder. To facilitate the exchange, the insert 194 may be provided with protrusions 196. Such an insert can advantageously also be used in all the other embodiments of the device described.

If desired, the receiving member 126 can be provided at the inner side thereof with one or more rotation prevention members 197 e.g. in the form of spikes and the like, as it is also shown in FIG. 28. The device may also include adjusting means 198 to set the distance between the holder 129 and the central longitudinal axis 171 of the receiving sleeve 131.

In the embodiment shown in FIG. 28, such an adjusting means comprises an internally threaded bush 199 integrated in the holder 129, with the axis of the bush being substantially perpendicular to the longitudinal central axis of the receiving member 126. A set screw 200 provided with a scale 201 is adapted to be screwed into the internally threaded bush 199.

Pursuant to FIGS. 29 to 31, either a part 203 carrying the receiving means 125 and/or a part 204 comprising the handle 130 may be detachably coupled with the remaining parts of the device. For this purpose the holder 129 e.g. has a section 205 which carries the pipe socket 133 and which includes a male projection 206 adapted to be inserted into a female member 207 of the holder part 204, wherein the male projection 206 and the female member 207 have complementary polygonal, e.g. square, outer and inner shapes, respectively. The male projection 206 and female member 207 have bores 208, 209, which are aligned with each other upon the male projection and female member being assembled, and a split pin 210, a fixing screw or the like is adapted to be inserted into them. In the embodiment of FIGS. 29 and 30 the holder part 203 is fitted with a head 212 having a through-bore 211, which head is adapted to be inserted between a pair of parallel holding lugs 213 of section 205 and to be fastened there by a wing nut 214. The wing nut 214, when in assembled state, extends through a bore of one of the holding lugs 213 corresponding to bore 211, and it is screwed into a corresponding threaded bore 215 of the other holding lug 213. The width of the head 212 may substantially match with the width of the gap 216 provided between the holding lugs 213 for receiving the head 212. The head 212, however, need not be as wide as the gap 216, and a spacer disk 217 held in its position by the screw 214 can be additionally inserted into the gap 216 on either side of the head 212. In the latter case, the central axis of the receiving means 125 will be disposed in a preset distance in parallel to the central longitudinal axis of the receiving sleeve 131 at one or the other side of this central longitudinal axis, dependent on which side of the head 212 the spacer disk 217 has been inserted. Thus it is easy to determine a predefined eccentricity between the central axis of the receiving means and the central longitudinal axis of the receiving sleeve 131.

FIG. 31 shows a modified embodiment of the holder section which is indicated at 205' and where the male projection 206 has been replaced with an externally threaded projection 216 with which the part 204 of the holder 129 comprising the handle 130 can be screwed together. The section 205' is provided at its in FIG. 31 upper side with a sleeve-shaped female member 219, into which the end 220 of the holder 203 averted from the receiving means 125 can be inserted. The holder 203 and section 205' can be mutually fixed again with the help of a wing nut 214 which is inserted into corresponding holes of the female member 219 and of the end 220 and which is screwed into a threaded bore in section 205' not shown in FIG. 31. If the end 220 of the holder 203 is of the same thickness as the height of the female member 219, the central axis of the receiving means 126 coincides with the central longitudinal axis 171 of the receiving sleeve 131. If, however, the thickness of the end 220, is made less than the height of the clamping element 219, similar to the embodiment of FIG. 29, a spacer disk 221 can be inserted together with the end 220 on either of its sides into the female member 219 to provide for a precisely defined offset between the central axis of the receiving means and the central longitudinal axis of the receiving sleeve.

In accordance with the modified embodiment of FIG. 32, the holder 129 also can be detachably or, as illustrated, integrally connected with a sensor 223. The sensor 223 may be designed as a condyle sensor or the like.

In the modified embodiment shown in FIG. 33 the pipe socket 133 attached to the holder 129 is provided with an internal thread 224. A receiving sleeve 131' which has an external thread 225 and is illustrated in FIG. 34 may be screwed into the threaded bore of pipe socket 133, wherein the receiving sleeve 131' is provided at the end opposite to the receiving means 125 with wing-shaped extensions 226 for the purpose of easy manipulation. In this embodiment the intermediate sleeve 140 can be omitted. By correspondingly advancing the receiving sleeve 131' the latter itself may be contacted with the bone system to thereby fix the device 120 with respect to the bone system. In view of the fact that the intermediate sleeve 140 is omitted, the repositioning sleeve 146 and the fixation sleeve 150 can also be dispensed with. If the diameter of the longitudinal opening 227 is adapted to the instrument diameter, the centering sleeve 158 can be left out as well.

FIG. 35 shows a receiving sleeve 131" of the type explained above with reference to FIG. 34 and having a longitudinal bore 227 the diameter of which is adapted to a Kirschner's wire 228. When using the receiving sleeve 131" of FIG. 35, the device 120 may be used to at first shoot a Kirschner's wire 228 into the bone system in an axially aligned manner. The device 120 can then be pulled off from the Kirschner's wire 228 which will remain in the bone system, and a hollow drill 229 which is shown in FIG. 36 and which has an internal longitudinal opening 230 adapted to the diameter of the Kirschner's wire 228 can be driven into the bone system whilst being guided by the Kirschner's wire 228.

FIG. 37 shows an instrument 232 having the shape of a chisel or plane and provided with a guiding pin 233 which, after making the drilling 122, may be inserted into the end of this drilling averted from the femoral head. The instrument 232 is further provided with a blade 234. The blade can be used to machine the end of the drilling 122 facing away from the femoral bone head by hammering onto the end 235 of the instrument 232. Thus particularly a bed for receiving the leaf spring 22 or an angled plate used instead of such a spring can be made up in a precise and simple way.

FIG. 38 shows a further modified embodiment of the surgical device in which the lateral holder 129 interconnecting the receiving means 125 and the receiving sleeve 131 may be rotated and longitudinally moved with respect to the receiving sleeve 131, but once set in position is secured against rotary movements. For this purpose a carrier section 237 firmly attached to the receiving sleeve 131 is equipped with a splined hub 238 which engages a splined shaft 239 at the end of the holder 129 facing away from the receiving member 126. The splined hub 238 is a part of a sleeve 240 which has a chamber 241 to house a compression spring 242. The compression spring 242 abuts with its one end the front surface of the splined shaft 239 and with the other end thereof a bottom 234 of the sleeve 240. A set screw 244 passes, in the assembled state, through a central hole 245 in the bottom 243, the compression spring 242, and splined shaft 238 down into a threaded opening 246 which is coaxial with the longitudinal axis of the splined shaft 239. When set screw 244 is tightened, the receiving means 125 is pulled against the resistance of the spring 242 in the direction towards the receiving sleeve 131. If the set screw is turned in opposite direction, the receiving means 125 will move away from the receiving sleeve 131 under the influence of spring 242. After having loosened the set screw 244 the splined shaft 238 can be pulled out entirely of the splined hub and reinserted in a different position in relation to the angle of splined shaft, to thereby reposition the central axis of the receiving member 126 and the longitudinal central axis of the receiving sleeve 131. The angular orientation of splined shaft 239 in relation to splined hub 238, in which the central axis of the receiving member 126 is aligned with the central longitudinal axis of the receiving sleeve 131 preferably can be marked with signs 246 and 248 on the outer side of the splined hub 238 and the splined, shaft 239, respectively. In the illustrated example the splined shaft 239 further is provided with a longitudinal scale 249.

FIG. 39 shows an embodiment of the surgical device where a sleeve 251 is taking over the role of the repositioning sleeve 146 and of the centering sleeve 158 of the embodiment shown in FIGS. 19 and 20. Sleeve 251 is provided with an external thread 252 and an actuating member 253. The diameter of a longitudinal central opening in the sleeve 251 is adapted to the outer diameter of the tool to be used (in particular the drill or wire) in order to provide for substantially clearance-free guiding. In this case the intermediate sleeve 140' has no external thread 144 but carries, at its outer circumference at the end remote from the crown 141 of spikes, a circular stop 255. When assembled, the circular stop 255 will contact an end of a compression spring 256 which is inserted into the receiving sleeve 131 and which surrounds the part of the intermediate sleeve 140 adjacent the circular stop 255. Concurrently, the second end of the compression spring 256 will press against a circular stop 257 at the inner circumference of the receiving sleeve 131. The externally threaded section 252 of the sleeve 251 engages an internally threaded section 258 of the receiving sleeve 131. By sufficiently screwing the sleeve 251 down into the receiving sleeve 131 the spiked crown 141 of the intermediate sleeve 140 can be contacted with the bone system and the device fixed as above mentioned.

Figure 40:
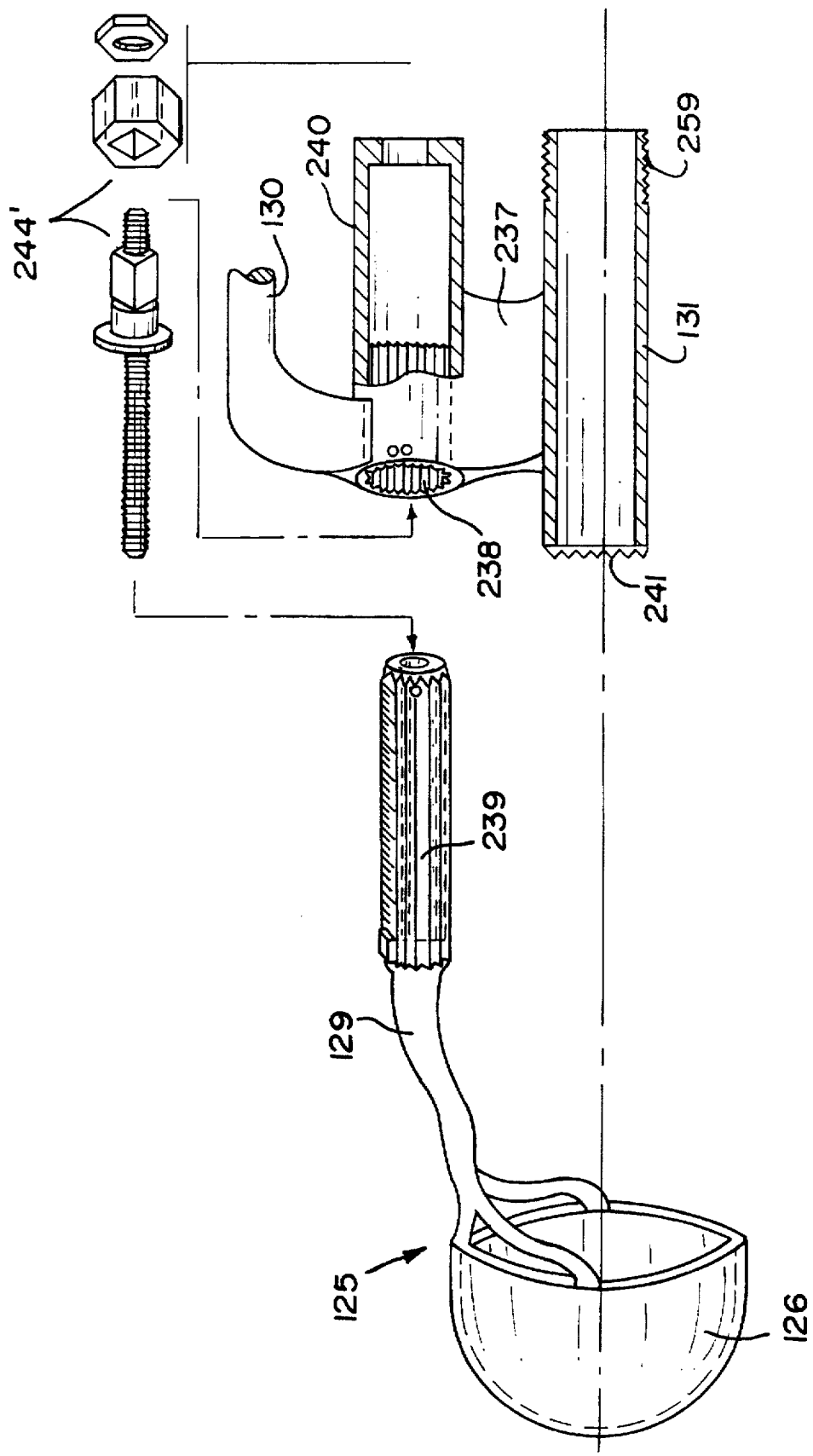
FIG. 40 is an exploded, partially perspective and partially sectional view of a simplified embodiment of the device.

The device illustrated in FIG. 40 corresponds to the embodiment of FIG. 38 as to the adjustable coupling between the receiving means 125 and receiving sleeve 131. The receiving sleeve 131 itself is in this case provided with the crown 141 of spikes, and the device can be fixed to the bone system by actuation of the set screw 244', wherein the spring 242 is omitted, but the set screw 244' will serve for relative longitudinal positioning of the receiving sleeve and the receiving member. The centering sleeve 158 can be screwed onto a threaded section 259 of the receiving sleeve 131. The internal diameter of the receiving sleeve 131 itself may be adapted to the outer diameter of the tool to be used. In this arrangement the centering sleeve also can be dispensed with.

Figure 41:
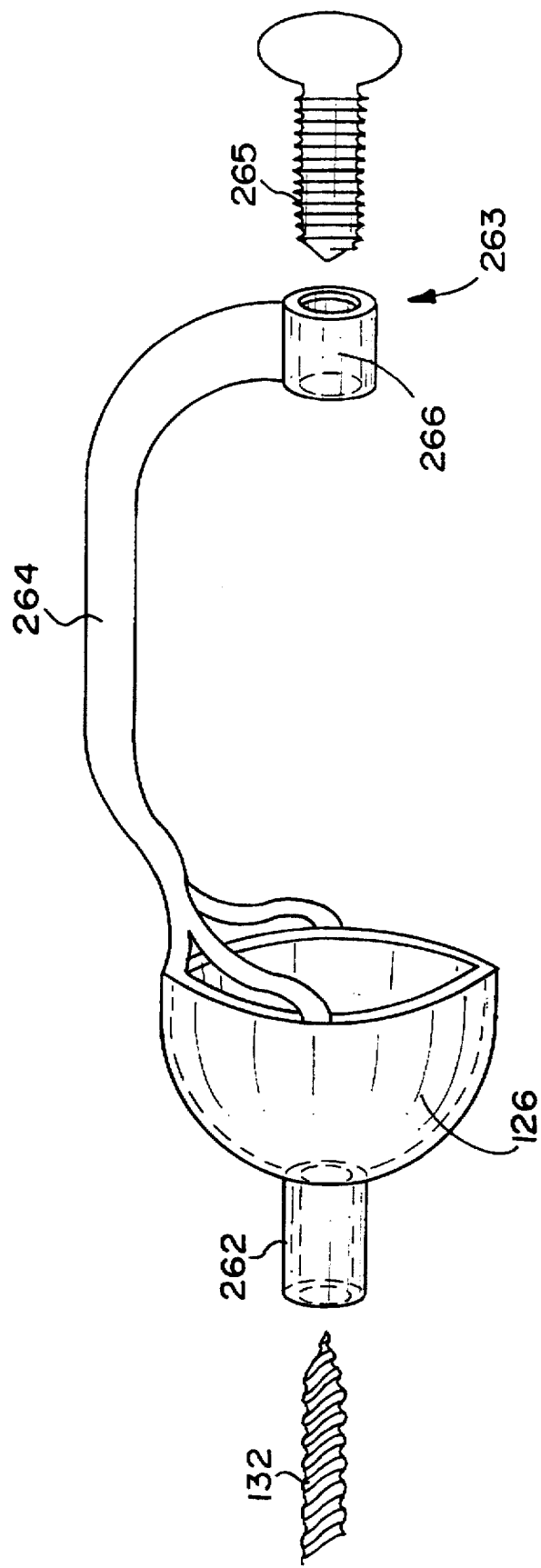
FIG. 41 is a perspective view of an embodiment of the device for forming the drilling from the side of the joint head.

FIG. 41 shows another embodiment of the surgical device where the receiving member 126 is provided with a guiding sleeve 262. The guiding sleeve 262 projects from the side of the receiving member 126 averted from a holding member 263 and extends along the longitudinal central axis of the receiving member 126. The receiving member 126 and the holding member 263 are interconnected by a lateral holder 264 whose central part can be simultaneously used as a handle. The holding member 263, in the case of the embodiment shown, has a fixation screw 265 which is to be screwed into a threaded sleeve 266 of the holder 264. The guiding sleeve 262 is used to guide a tool, such as the drill 132, wherein in this case the drilling is made from the side of the joint head.

It is to be understood that numerous other alternatives can be devised. Thus for example rotation prevention members 197 may be provided at the inner side of the receiving member 126 also in the embodiments depicted in FIGS. 38, 40, and 41. The shank of the drill, as well as the inner surface of the guiding part of the centering sleeve, or of the receiving sleeve can be threaded, wherein the interengagement of the threadings has the effect that a rotation of the drill automatically will result in a longitudinal movement of the drill. Additionally, the receiving sleeve can be mounted on the holder by means of an adjustable guiding pin and sleeve device.

As to the prosthesis, the flexible member 40 can be associated to either the cap-side or the supporting member-side telescopic member. Also a plurality of flexible members may be present. The hinge between the telescopic arrangement and the supporting member optionally can be dispensed with, or means may be provided for a temporary stiffening of an existing hinge, like in the course of recovery after femur bone fractures or in the case of osteoporosis. Such a stiffening e.g. can be reached by attaching to the supporting member 16 a locking plate carrying a male member adapted to be introduced into the end of the telescopic arrangement facing the supporting member.

In the embodiment of the joint prosthesis shown in FIG. 42 the female member 18', similar to the embodiment of FIG. 4, is disposed at the side of the cap. However, channel 49 is missing. In order to allow the coupling means or snap-in locking means 30 to be selectively engaged and disengaged from the side of the supporting member, spring arms 55 in accordance with FIG. 5 are placed on the male member 17', and these spring arms can be displaced in outward direction by a threaded pin 270 which is adapted to be actuated form the side of the supporting member. For this purpose the threaded pin 270 is fitted at its right end, as viewed in FIG. 42, with external threads 271 which will be screwed into internal threads 272 of an axial through channel 273 of the male member 17'. By advancing threaded pin 270, spring arms 55 are spread out; thereby they are engaged with the snap-in recesses of contact surface 37 on the internal side of female member 18', which contact surface is shaped like saw teeth or is provided with any other suitable profile, or is without any profile. If, however, the threaded pin 270 is being screwed outwards, the spring arms 55, under the influence of the biasing force of the spring, will automatically be displaced in an inward direction and thus will be disengaged from the latching recess on the contacting surface 37.

In the embodiment of FIG. 43a a spring 31" similar to spring 31' in FIG. 2 is provided, which spring 31" additionally includes an internally threaded section 275. The spring arms 46 of spring 31" can be spread out by inserting a threaded pin 276 into the axial channel 273 of male member 17' from the side of the supporting member, and by engaging an externally threaded section 277 of pin 276 with the internally threaded section 275.

FIG. 43b shows an embodiment in which the hinge 19' includes pivot arms projecting from the supporting member 16 towards the female member 18. Female member 18 is hingedly connected with these pivot arms. This embodiment permits the hinge to be flush countersunk in the outer mouth of the bore provided in the femoral head.

Female member 18 or 18', respectively, e.g. can be manufactured from a cylindrical sleeve having a circular cross-section, into which sleeve internal threads are cut. Subsequently the sleeve can be brought into a polygonal, for example hexagonal, shape.

I claim:

1. A joint prosthesis for a joint head of a joint, which head cooperates with a joint cavity, said prosthesis comprising:

a cap having a contact surface adapted to abut the joint head, and having an outer surface which is at least approximately shaped as a spherical cap;

a telescopic arrangement having a first telescopic member linked with the cap and projecting from the cap, and a second telescopic member which is in telescopic engagement with said first telescopic member, said telescopic arrangement being sized and arranged so as to pass through a drilling in the joint head and bone regions adjacent thereto when in an implanted state, and a supporting member attached to said second telescopic member and designed for fixation to a bone surface of a bone located opposite to the joint head, wherein the first telescopic member is guided for sliding movement in relation to the second telescopic member in a direction away from the joint cavity, wherein said contact surface is defined by an internal surface of the cap, which internal surface is at least approximately adapted to the shape of the joint head, and wherein said prosthesis comprises restraining means the operation of which is dependent on the direction of the forces acting thereon so as to permit changes in position of the cap with respect to the supporting member in the direction away from the joint cavity, and to at least impede changes in position of the cap with respect to the supporting member in the direction towards the joint cavity in comparison with the changes of position in the direction away of the joint cavity.

2. The joint prosthesis of claim 1, wherein said restraining means is designed to prevent changes in position of the cap with respect to the supporting member in the direction towards the joint cavity.

3. The joint prosthesis of claim 1, wherein said telescopic arrangement is designed so that the joint prosthesis, in its implanted state, at least partly permits biomechanical movements of the joint head and joint neck relative to the bone carrying the joint head and joint neck.

4. The joint prosthesis of claim 3, wherein said telescopic arrangement has a flexibility permitting biomechanical movements of the joint head and joint neck relative to the bone carrying the joint head and joint neck.

5. The joint prosthesis of claim 1, wherein the internal surface of the cap is at least approximately shaped like a spherical cap.

6. The joint prosthesis of claim 1, wherein said supporting member is comprised of a supporting plate which is attached to the end of the second telescopic member remote from the cap.

7. The joint prosthesis of claim 1, wherein said second telescopic member is pivotally connected to said supporting member.

8. The joint prosthesis of claim 7, wherein said second telescopic member is connected to said supporting member by means of a hinge having a hinge axis which is substantially perpendicular to the longitudinal extension of said telescopic arrangement and substantially perpendicular to the longitudinal extension of the supporting member.

9. The joint prosthesis of claim 8, wherein said hinge is designed for being sunk in said drilling.

10. The joint prosthesis of claim 7, wherein said second telescopic member is connected to said supporting member by means of a hinge having a hinge axis which is substantially perpendicular to the longitudinal extension of said telescopic arrangement and substantially parallel to the longitudinal extension of the supporting member.

11. The joint prosthesis of claim 7, wherein said second telescopic member is elastically spring-supported on the supporting member.

12. The joint prosthesis of claim 7, further comprising locking means for selectively stiffening the pivotal connection between the second telescopic member and the supporting member.

13. The joint prosthesis of claim 12, wherein said second telescopic member is elastically spring-supported on the supporting member; and
wherein the spring-elastic support means of the second telescopic member comprises a leaf spring leaning against the second telescopic member and the supporting member, and wherein the locking means is comprised of an angled plate, which is interchangeable with said leaf spring.

14. The joint prosthesis of claim 1, wherein said telescopic arrangement is equipped with at least one flexible member at least partially permitting biomechanical movements of the joint head.

15. The joint prosthesis of claim 14, wherein said flexible member is placed in a distance from the internal surface of the cap corresponding to about one to three times an inner diameter of the cap.

16. The joint prosthesis of claim 14, wherein said flexible member is designed to prevent twisting motion.

17. The joint prosthesis of claim 14, wherein said flexible member is selected from the group comprising a spring adapted to prevent torsion, a flexible shaft, a wire mesh shaft, a spring joint and a flexible insert.

18. The joint prosthesis of claim 14, wherein said flexible member is integrally connected with said first telescopic member.

19. The joint prosthesis of claim 1, wherein at least one of said telescopic members is made of at least two parts disposed substantially one behind the other in the longitudinal direction of the telescopic arrangement, said parts being mutually engaged in a manner preventing twisting motion and being adapted to be secured against spontaneous releasing.

20. The joint prosthesis of claim 1, wherein said restraining means comprises automatic, direction-dependent coupling means.

21. The joint prosthesis of claim 1, wherein said restraining means is selected from the group consisting of snap-in locking means, detent means and spring-loaded restraining means.

22. The joint prosthesis of claim 21, wherein said restraining means has at least one outstanding protrusion on one of said telescopic members, said protrusion being disposed so as to lockingly engage a contacting surface on the other one of said telescopic members when said first telescopic member is attempted to be displaced relative to said second telescopic member in the direction towards the joint cavity, but to allow displacement of said first telescopic member relative to said second telescopic member in the direction away from the joint cavity.

23. The joint prosthesis of claim 22, wherein said protrusion consists of at least one spring member one end of which is in fixed connection with said one telescopic member and the other end of which is free to move and is biased in radial direction.

24. The joint prosthesis of claim 22, and comprising a ring adapted to be pulled over said protrusion for at first holding back the protrusion and for automatically releasing the protrusion upon said telescopic members having been inserted into each other.

25. The joint prosthesis of claim 22, wherein said contacting surface comprises a plurality of saw-tooth shaped recesses.

26. The joint prosthesis of claim 22, wherein said contacting surface is defined by a coating into which said protrusion is adapted to dig itself.

27. The joint prosthesis of claim 1, and comprising spring biasing means for biasing said first telescopic member in the direction away from the joint cavity.

28. The joint prosthesis of claim 27, wherein said spring biasing means comprises at least one tractive spring one end of which is attached to said first telescopic member and the other end of which is attached to one of said second telescopic member and said supporting member.

29. The joint prosthesis of claim 27, wherein said spring biasing means also defines said restraining means.

30. The joint prosthesis of claim 27, wherein one of said telescopic members is a male member having an external shoulder, and the other of said telescopic members is a female member having an internal shoulder, and wherein a biasing spring is disposed between said shoulders.

31. The joint prosthesis of claim 30, wherein said male telescopic member comprises a pair of detachably interconnected coaxial parts one of which is attached to the cap and the other of which is provided with said external shoulder.

32. The joint prosthesis of claim 1, further comprising means for disabling said restraining means when disassembling the prosthesis.

33. The joint prosthesis of claim 30, wherein said first telescopic member substantially centrically projects from the internal surface of the cap.

34. The joint prosthesis of claim 1, further comprising anti-twist means for preventing rotary motion of the cap relative to the joint head.

35. The joint prosthesis of claim 34, wherein said telescopic members are interconnected in a manner preventing relative twisting of said telescopic members.

36. The joint prosthesis of claim 35, wherein said telescopic members are profiled to provide for twist-proof mutual interconnection of said telescopic members.

37. The joint prosthesis of claim 34, wherein said first telescopic member is placed eccentrically in a predetermined distance from a central axis of the cap.

38. The joint prosthesis of claim 1, further comprising a sleeve adapted to be inserted into said drilling, said sleeve embracing said telescopic arrangement along at least a portion of its longitudinal dimension, when said prosthesis is in an implanted state.

39. The joint prosthesis of claim 1, wherein the telescopic arrangement has a circular outer perimeter at least for a length thereof extending through the cap.

40. The joint prosthesis of claim 1, wherein the cap has a rim which is shaped and disposed to at least prevailingly lie within a plane inclined with respect to a longitudinal axis of the prosthesis at such an angle, that the cap, when implanted, is adapted to overlap the joint head at least approximately evenly.

41. The joint prosthesis of claim 1, wherein the cap is equipped with recesses.

42. The joint prosthesis of claim 1, further comprising at least one insert adapted to be inserted into the cap as an internal part thereof, said insert having an inner surface defining a contact surface which is at least approximately adapted to the shape of the joint head, and said insert being adapted to be selected from a group of inserts differing in at least one of wall thickness and shape.

43. The joint prosthesis of claim 42, wherein said insert has an opening for receiving said first telescopic member.

44. The joint prosthesis of claim 1, wherein said cap includes an upper cap portion which is rotatably mounted on a lower cap portion.

45. The joint prosthesis of claim 1, wherein said cap includes a flattened pole.

46. A joint prosthesis for a joint head of a joint, which head cooperates with an joint cavity, said prosthesis comprising:

a cap having a contact surface adapted to abut the joint head, and having an outer surface which is at least approximately shaped as a spherical cap, said contact surface being defined by an internal surface of the cap, which internal surface is at least approximately adapted to the shape of the joint head;

at least one supporting member designed for fixation to a bone surface of a bone located opposite to the joint head; and at least one restraining means for impeding relative movement between the cap and the supporting member in the direction towards the joint cavity in comparison with relative movement in the direction away of the joint cavity, said restraining means having at least one elastic traction member arranged so as to pass through a drilling in the joint head and bone regions adjacent thereto when in an implanted state, said traction member having one end thereof attached to the cap and having the other end thereof connected to the supporting member, and said traction member biasing the cap in the direction away from the joint cavity.

47. The joint prosthesis of claim 46, wherein said traction member is a spring member.

48. The joint prosthesis of claim 46, wherein at least one stem projects from the inner surface of the cap, and wherein said traction member engages the end of the stem averted from the inner surface of the cap.

49. The joint prosthesis of claim 48, further comprising a sleeve adapted to be inserted into said drilling, said sleeve embracing at least one of said traction member and said stem along at least a portion of their longitudinal dimensions, when said prosthesis is in an implanted state.

50. The joint prosthesis of claim 48, further comprising a sleeve adapted to be inserted into said drilling, said sleeve embracing at least one of said traction member and said stem along at least a portion of their longitudinal dimensions, when said prosthesis is in an implanted state; and wherein said insert and said sleeve are firmly interconnected.

51. The joint prosthesis of claim 46, further comprising at least one insert adapted to be inserted into the cap as an internal part thereof, said insert having an inner surface defining a contact surface which is at least approximately adapted to be selected from a group of inserts differing in at least one of wall thickness and shape.

52. The joint prosthesis of claim 46, wherein the prosthesis is a hip joint prosthesis for a femoral head which cooperates with an acetabulum.

53. The joint prosthesis of claim 1, wherein the prosthesis is a hip joint prosthesis for a femoral head which cooperates with an acetabulum.

* * * * *